United States Patent [19]

Daynes et al.

[11] Patent Number: 5,753,237

[45] Date of Patent: *May 19, 1998

[54] METHOD FOR AUGMENTING IMMUNOLOGICAL RESPONSES

[75] Inventors: Raymond A. Daynes, Park City; Barbara A. Araneo, Salt Lake City, both of Utah

[73] Assignee: University of Utah Research Foundation, Salt Lake City, Utah

[*] Notice: The term of this patent shall not extend beyond the expiration date of Pat. No. 5,518,725.

[21] Appl. No.: 309,704

[22] Filed: Sep. 21, 1994

Related U.S. Application Data

[62] Division of Ser. No. 219,418, Mar. 29, 1994, abandoned, which is a continuation of Ser. No. 779,499, Oct. 18, 1991, abandoned, which is a continuation-in-part of Ser. No. 412,270, Sep. 25, 1989, abandoned.

[51] Int. Cl.$^6$ .............. A61K 31/56; A61K 31/59; A61K 39/00
[52] U.S. Cl. .............. 424/278.1; 514/167; 514/169
[58] Field of Search .............. 424/278.1, 283.1; 514/167, 169

[56] References Cited

U.S. PATENT DOCUMENTS

| | | | |
|---|---|---|---|
| 4,110,446 | 8/1978 | DeLuca et al. | 514/167 |
| 4,341,774 | 7/1982 | Aoki et al. | 514/167 |
| 4,496,556 | 1/1985 | Orentreich et al. | 514/178 |
| 4,507,289 | 3/1985 | Coleman et al. | 514/170 |
| 4,518,595 | 5/1985 | Coleman et al. | 514/178 |
| 4,542,129 | 9/1985 | Orentreich | 514/178 |
| 4,602,008 | 7/1986 | Krsek | 514/178 |
| 4,617,299 | 10/1986 | Knepper | 514/178 |
| 4,628,052 | 12/1986 | Peat | 514/171 |
| 4,666,898 | 5/1987 | Coleman et al. | 514/177 |
| 4,698,221 | 10/1987 | Straub | 424/245.1 |
| 4,789,658 | 12/1988 | Yoshimoto et al. | 514/2 |
| 4,898,694 | 2/1990 | Schwartz et al. | 552/505 |
| 4,956,355 | 9/1990 | Prendergast | 514/178 |
| 4,980,358 | 12/1990 | Smith | 514/288 |
| 5,000,956 | 3/1991 | Amkraut et al. | 424/434 |
| 5,077,284 | 12/1991 | Loria et al. | 514/171 |
| 5,206,008 | 4/1993 | Loria | 424/45 |
| 5,407,684 | 4/1995 | Loria et al. | 424/442 |
| 5,518,725 | 5/1996 | Daynes et al. | 424/212.1 |
| 5,540,919 | 7/1996 | Daynes et al. | 424/85.2 |
| 5,562,910 | 10/1996 | Daynes et al. | 424/278.1 |

FOREIGN PATENT DOCUMENTS

| | | |
|---|---|---|
| 0 133 995 | 8/1984 | European Pat. Off. |
| 0 282 156 | 1/1988 | European Pat. Off. |
| 55-139320 | 4/1979 | Japan. |
| WO 91/04030 | 4/1991 | WIPO. |

OTHER PUBLICATIONS

Callard et al Immunology Today (1990) vol. 11, 200–203.

Ben-Nathan, D. et al. (1992). "Dehydroepiandrosterone Protects Mice Inoculated with West Nile Virus and Exposed to Cold Stress." *J. Med. Virol.* 38:159–166.

Araneo, B. et al. (1991). "Dihydrotestosterone Exerts a Depressive Influence on the Production of Interleukin-4 (IL-4), IL-5 and γ-Interferon, but not IL-2 by Activated Murine T Cells." *Blood* 78:3, pp. 688–699.

Meikle, A. et al. (1991). "Adrenal Androgen Secretion and Biologic Effects." *Endocrinol. Metab. Clin. N. Am.* 29:2, pp. 381–400.

Suzuki, T. et al. (1991). "Dehydroepiandrosterone Enhances IL2 Production and Cytotoxic Effector Function of Human T Cells." *Clin. Immunol. Immunopathol.* 61:202–211.

Wiedmeier, S. et al. (1991). "Thymic Modulation of IL-2 and IL-4 Synthesis by Peripheral T Cells." *Cell. Immunol.* 135:501–518.

Wu, C.Y. et al. (1991). "Glucocorticoids Supress the Production of Interleukin 4 by Human Lymphocytes." *Eur. J. Immunol.* 21:2645–2647.

Daynes, R. et al. (1991). "Locally Active Steroid Hormones may Facilitate Compartmentalization of Immunity by Regulating the Tyes of Lymphokines Produced by Helper T Cells." *Res. Immunol.* 142:40–45.

van der Heliden, P. et al. (1991). "Manipulation of Intestinal Immune Responses Against Ovalbumin by Cholera Toxin and its B Subunit in Mice." *Immunol.* 72:89–93.

Lemire, J. et al. (1991). "1,25-Dihydroxyvitamin $D_3$ Prevents the In Vivo Induction of Murine Experimental Autoimmune Encephalomyelitis." *J. Clin. Invest.* 87:1103–1107.

Finkelman, R. et al. (1991). "Vitamin D Deficiency Causes a Selective Reduction in Deposition of Transforming Growth Factor β in Rat Bone: Possible Mechanism for Impaired Osteoinduction." *Proc. Nat. Acad. Sci. USA* 88:3657–3660.

Daynes, R. et al. (1990). "Regulation of Murine Lymphokine Production In Vivo: II. Dehydroepiandrosterone is a Natural Enhancer of Interleukin 2 Synthesis by Helper T Cells." *Eur. J. Immunol.* 20:4, pp. 793–802.

Daynes, R. et al. (1990). "Regulation of Murine Lymphokine Production In Vivo: III. The Lymphoid Tissue Microenvironment Exerts Regulatory Influences over T Helper Cell Function." *J. Exp. Med.* 171:979–9961.

Finkelman, F. et al. (1990). "Lymphokine Control of In Vivo Immunoglobulin Isotype Selection." *Ann. Rev. Immunol.* 8:303–333.

Mbawuike, I. et al. (1990). "Enhancement of the Protective Efficacy of Inactivated Influenza A Virus Vaccine in Aged Mice by IL-2 Liposomes." *Vaccine* 8:347–352.

Risdon, G. et al. (1990). Mechanisms of Chemoprevention by Dietary Dehydroisoandrosterone: Inhibition of Lymphopoiesis,: *Am. J. Pathol.* 136:4, pp. 759–769.

(List continued on next page.)

*Primary Examiner*—Mary E. Mosher
*Attorney, Agent, or Firm*—Venable, Baetjer, Howard & Civiletti, LLP

[57] ABSTRACT

Methods for augmenting immune responses in immunodeficient individuals are disclosed. The methods utilize steroid hormones, particularly DHEA, its prohormones (particularly DHEA-S), and DHEA-cogeners. Additional embodiments of the invention include pharmaceutical compositions for use in the methods.

28 Claims, 21 Drawing Sheets

OTHER PUBLICATIONS

May, M. et al. (1990). "Protection from Glucocorticoid Induced Thymic Involution by Dehydroepiandrosterone," *Life Sciences* 46:1627–1631.

Ledman, D. et al. (1990). "Mechanism for Transforming Growth Factor β and IL–2 Enhancement of IgA Expression in Lipopolysaccharide–Stimulated B Cell Cultures," *J. Immunol.* 144:952–959.

Brown, S. et al. (1990). "Neuroendocrine Immune Interactions," *Immunophysiology: The Role of Cells and Cytokines in Immunity and Inflammation,* J. Oppenheim, Eds., Oxford University Press, N.Y., pp. 306–319.

Khansari, D. et al. (1990). "Effects of Stress on the Immune System," *Immunol. Today* 11:5, pp. 170–175.

Wira, C.R. et al. (1990). "Glucocorticoid Regulation of the Humoral Immune System I: In vivo Effects of Dexamethasone on IgA and IgG in Serum and at Mucosal Surfaces," *J. Immunol.* 144:1, pp. 142–146 [Abstract].

May, M. et al. (1990). "Protection from Glucocorticoid Induced Thymic Involution by Dehydroepiandrosterone," *Life–Sci.* 46:22, pp.1627–1631 [Abstract].

Matsunaga, A. et al. (1989). "Dehydroisoandrosterone Prevention of Autoimmune Disease in NZB/W F1 Mice: Lack of an Effect on Associated Immunological Abnor–malities," *Biochim. Biophys. Acta* 992:3, pp. 265–271.

Abe, J. et al. (1989). "A Synthetic Analogue of Vitamin $D_3$, 22–Oxa–1α, 25–Dihydroxy–Vitamin $D_3$, is a Potent Modulator of In Vivo Immunoregulating Activity Without Inducing Hypercalcemia in Mice," *Endocrinol.* 124:5, pp. 2645–2647.

Bhalla, A.K. (1989). "Hormones and the Immune Response," *Ann. Rheum. Dis.* 48:1–6.

Coffman, R. et al. (1989). "T–Helper Heterogeneity and Immune Response Patterns," *Hosp. Pract.*, Aug. 15, 1989, pp. 101–133.

Daynes, R. et al. (1989). "Contrasting Effects of Glucocorticoids on the Capacity of T Cells to Produce the Growth Factors Interleukin 2 and Interleukin 4," *Eur. J. Immunol.* 19:2319–2325.

Rogers, W. et al. (1989). "Dehydroepiandrosterone Protection Against Dexamethasone Induced Thymic Involution: Flowcytometric and Mechanistic Studies," *The Endocrine Society: Program & Abstracts,* No. 668, p. 189 [Abstract].

Dolecek, R. (1989). "Endocrine Changes After Burn Trauma—A Review," *Keio J. Med.* 38:3 pp. 262–276.

Rigby, W. (1988) "The Immunobiology of Vitamin D," *Immunol. Today* 9:2, pp. 54–57.

Loria, R. et al. (1988). "Protection Against Acute Lethal Viral Infections with the Native Steroid Dehydroepiandrosterone (DHEA)," *J. Med. Virol.* 26:301–314.

Kalimi, M. et al. (1988). "Physiochemical Characterization of [$^3$H] DHEA Binding in Rat Liver," *Biochem. Biophys. Res. Communicats.* 156:1, pp. 22–29.

Regelson, W. et al. (1988). "Hormonal Intervention: Buffer Hormones or State Dependency: The Role of Dehydroepiandrosterone (DHEA), Thyroid Hormone, Estro–gen and Hypophysectomy in Aging," *Ann. N.Y. Acad. Sci.* 518:260–273.

Boger, J. et al. (1988). "Immodulatory Approaches to the Treatment of Inflammation," *Ann. Reps. Med. Chem.* 23:171–180.

Dinarello, C. et al. (1987). "Current Concepts: Lymphokines," *N. Eng. J. Med.* 317:15, pp. 940–945.

Mestecky, J. (1987). "The Common Mucosal Immune System and Current Strategies for Induction of Immune Responses in External Secretions," *J. Clin. Immunol.* 7:4, pp. 265–276.

Petkovich, P. et al. (1987). "1,25–Dihydroxyvitamin $D_3$ Increases Epidermal Growth Factor Receptors and Transforming Growth Factor β–Like Activity in a Bone–Derived Cell Line," *J. Biol. Chem.* 262:28, pp. 13424–13428.

Pfeilschifter, J. et al. (1987). "Modulation of Type β Transforming Growth Factor Activity in Bone Cultures by Osteotropic Hormones," *Proc. Nat. Acad. Sci. USA* 84:2024–2028.

Matsushima, K. et al. (1987). "Phosphorylation of a Cytosolic 65–kDa Protein Induced by Interleukin 1 in Glucocorticoid Pretreated Normal Human Peripheral Blood Mono––nuclear Leukocytes," *J. Immunol.* 1393367–3374.

Knabbe, C. et al. (1987). "Evidence That Transforming Growth Factor–β is a Hormonally Regulated Negative Growth Factor in Human Breast Cancer Cells," *Cell* 48:417–428.

Roberts, E. et al. (1987). "Effects of Dehydroepiandrosterone and its Sulfate on Brain Tissue in Culture and on Memory in Mice," *Brain Res.* 406:357–362.

Gordon, G. et al. (1987). "Modulation of Growth, Differentiation and Carcinogenesis by Dehydroepiandrosterone," *Adv. Enz. Regul.* 26:355–378.

Tabata, T. et al. (1986). "The Effect of 1α–Hydroxyvitamin $D_3$ on Cell–Mediated Immunity in Hemodialyzed Patients," *J. Clin. Endocrinol. Metab.* 63:1218–1221.

Lucas, J. et al. (1985). "Prevention of Autoantibody Formation and Prolonged Survival in New Zealand Black/New Zealnd White F1 Mice Fed Dehydroisoandrosterone," *J. Clin. Invest.* 75:2091–2093.

Komori, T. et al. (1985). "The Effect of 1α–Hydroxyvitamin $D_3$ on Primary Antibody Formation in Mice," *Immunopharmacol.* 9:141–146.

Nakao, Y. et al. (1985). "Effect of Active Vitamin $D_3$ on Age–Related Immunological Changes," *J. Nutr. Sci. Vitaminol.* 31:49–57.

Gray, T. et al. (1985). "Vitamin D, Phagocyte Differentiation and Immune Function," *Surv. Immunol. Res.* 4:3, pp. 200–212.

Corman, L.C. (1985). "Effects of Specific Nutrients on the Immune Response: Selected Clinical Applications," *Med. Clin. N. Am. (US)* 69:4, pp. 759–791.

Schwartz, A. (1985). "The Effects of Dehydroespiandrosterone on the Rate of Development of Cancer and Autoimmune Processes in Laboratory Rodents," *Basic Life Sci. (US)* 35:181–191.

Weindruch, R. et al. (1984). "Food Intake Reduction and Immunological Alterations in Mice Fed Dehydrorepiandrosterone," *Exp. Gerontol.* 19(5):297–304.

Orentreich, N. et al. (1984). "Age Changes and Sex Differences in Serum Dehydroespiandrosterone Sulfate Concentrations Throughout Adulthood," *J. Clin. Endocrin. Metab.* 59:3, pp. 551–555.

Feher, K. et al. (1983). "Adrenocortical Function in Bronchial Asthma," *Acta–Med–Hung.* 40:2–3, pp. 125–131.

Bienenstock, J. et al. (1982). "Regulation of Lymphoblast Traffic and Localization in Mucosal Tissues, with Emphasis on IgA," *Fed. Proceeds.* 42:15, pp. 3213–3217.

Adolf, G. et al. (1979). "Glucocorticoid Hormones Inhibit DNA Synthesis and Enhance Interferon Production in a Human Lymphoid Cell Line," *Nature* 282:736–738.

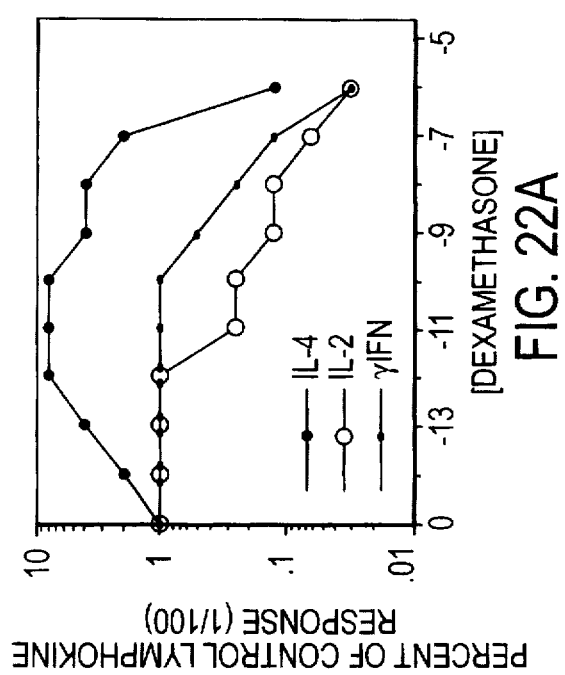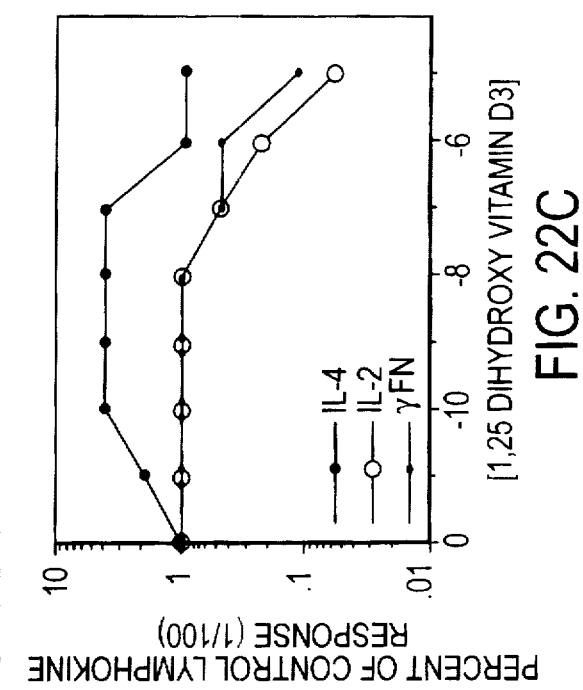
FIG. 22A
FIG. 22B
FIG. 22C

METHOD FOR AUGMENTING IMMUNOLOGICAL RESPONSES

CROSS-REFERENCE TO RELATED APPLICATION

This Application is a division of U.S. Ser. No. 08/219,418 which was filed on 29 Mar. 1994, now abandoned, which in turn is a continuation of U.S. Ser. No. 07/779,499 which was filed on 18 Oct. 1991, now abandoned, which in turn is a continuation-in-part of U.S. application Ser. No. 07/412,270 filed Sep. 25, 1989, now abandoned, the specification of which are incorporated by reference herein in their entirety.

TECHNICAL FIELD

The invention relates to methods and compositions used for the augmentation of an immune response in vivo and in vitro by the use of steroid hormones, more specifically, by the use of dehydropepiandrosterone (DHEA), dehydroepiandrosterone sulfate (DHEA-S), and analogs thereof.

BACKGROUND

Immunosuppression in animals can result from a depressed capacity to produce species of lymphokines which are essential to the development of protective forms of immunity. Imbalances between various types of lymphokines, where species of lymphokines capable of promoting one form of immune response exhibit enhanced production, while those lymphokines needed to promote protective forms of immunity are suppressed, can also lead to immunosuppression. Individuals may be immunosuppressed as a consequence of endogenous elevations in adrenal glucocorticosteroid (GCS) levels. This condition could result from viral infections, from certain bacterial infections, certain parasitic infections, cancer, some autoimmune syndromes, and stress and trauma, or as a secondary consequence to any clinical condition that causes an elevated production of interleukin-1 (IL-1). Plasma glucocorticoid steroid levels also can be elevated exogenously as a consequence of therapeutic treatment for a variety of clinical conditions. In addition to the above, it is also well known that certain essential functions of the immune system decline with age, a situation which correlates with elevations in adrenal output of glucocorticoid steroids and depressions in production of other types of adrenal steroid hormones.

It is known that lymphocytes exported from the thymus undergo a series of differentiation events which confer upon them the capacity to recognize and respond to specific peptide antigens presented appropriately in the context of self major histocompatibility complex (MHC) molecules. Mechanistically, thymic maturation is a complex process which includes an irreversible rearrangement of T cell receptor genes, the cell surface expression of these gene products as disulfide-linked heterodimers, positive and negative selection processes to provide appropriate restriction and avoidance of self-reactivity, and the synthesis and expression of CD4 or CD8 as accessory adhesion molecules. Microenvironmental influences within the thymus play an essential role in the fidelity of this process.

Subsequent to leaving the thymic micro-environment, mature T lymphocytes gain access to the recirculating T cell pool where they move freely via the blood between mucosal and nonmucosal lymphoid compartments in the mammalian host (Hamann et al. (1989), Immunol. Rev. 108:19). T-lymphocyte expression of lymphoid tissue-specific homing receptors, which are complementary for vascular addressins on high endothelial venules present in Peyer's patches and peripheral lymph nodes, provide a biochemical means for selectivity to this recirculation process (id.). Non-activated lymphocytes can move freely between mucosal and nonmucosal lymphoid tissues due to the presence of both types of homing receptors on their plasma membranes (Pals et al. (1989), Immunol. Rev. 108:111). Effector lymphocytes, and antigen-activated immunoblasts which are stimulated in a particular site in the body, however, exhibit a far more selective migratory behavior. These cells move primarily to tissues originally involved in antigen exposure and cellular activation (Hamann et al. (1989), supra; Pals et al. (1989), supra.).

An immune response is initiated following T cell recognition of antigen peptides in the context of self MHC molecules and generally takes place in one of the host's secondary lymphoid compartments. Cellular activation is triggered by the binding of antigen to the T cell receptor (TCR), forming an antigen/TCR complex which transduces the antigen-specific extracellular stimulation across the plasma membrane, and generates intracellular signals which include the activation of protein kinase C and the increases in intracellular calcium. While signal transduction can lead to T cell unresponsiveness, positive signal transduction events trigger a series of additional biochemical processes. One consequence of this activation is the stimulated production of a number of biologically active molecules which are collectively termed lymphokines. (See, Alcover et al. (1987), Immunol. Rev. 95:5; Gelfand et al (1987), Immunol. Rev. 95:59).

The lymphokines, many of which function primarily through autocrine and paracrine mechanisms, serve to mediate numerous effector functions controlled by T cells through their capacity to regulate cellular proliferation, differentiation, and maturation events in lymphocytes, plus other hematopoietic and somatic tissue cells (Paul (1989), Cell 57:521).

Each of the various types of lymphokines exhibit pleiotropic activities, dependent upon the specific type of cellular targets being stimulated. The biological evaluation of recombinant forms of specific lymphokines has determined that individual species can possess both distinct and overlapping cellular activities (Paul (1989), supra). Interleukin-2 (IL-2) and interleukin-4 (IL-4), for example, share the capacity to facilitate T cell growth but are disparate in their relative contribution to cellular and humoral immune responses. Cloned T cell lines, restricted in their capacity to produce individual species of lymphokines, have been described which demonstrate unique capabilities in serving as effector cells or helper cells for various immune responses (Paul (1989), supra; Hayakawa et al. (1988), J. Exp. Med. 168:1825; Mossman et al. (1989), Ann. Rev. Immunol. 7:145).

Treatment of individuals for immunosuppression has been focused on the use of purified lymphokines, usually IL-2, to restore normal propagation of T cells. Illustrative of this are the disclosures of U.S. Pat. No. 4,661,447 (issued Apr. 28, 1987 to Fabricus et al.), U.S. Pat. No. 4,780,313 (issued Oct. 25, 1988 to Koichiro et al.), and U.S. Pat. No. 4,789,658 (issued Dec. 6, 1988 to Yoshimoto et al.). However, the systemic administration of IL-2 for therapeutic purposes has numerous side effects. These side effects include fever, hypotension, hepatic and renal failure, myocardial infarctions, capillary leak syndrome, and massive edema (Dinatello et al. (1987), New England J. Med. 317:940.

Applicants' invention embodies methods for treating immunosuppression which are without the side-effects found with the purified lymphokines. These methods utilize the androgen steroid hormones, more specifically dehydroepiandrosterone (DHEA), the sulfated derivative thereof (DHEA-S), and analogs thereof.

DHEA is steroid hormone that has been extensively studied for many years. It has been reported to be involved in a wide variety of physiologic, immunologic, and pathologic conditions (for reviews, see Regelson et al. (1988), Ann. N.Y. Acad. Sci. 521:260; Gordon et al. (1986), Adv. Enzyme Reg. 26:355–382). Most endocrinologists believe that the primary function of DHEA is to serve as a precursor for the synthesis of testosterone and the estrogens by the gonads. The biosynthetic relationship of DHEA to other steroid hormones is shown in FIG. 1 (taken from Cook and Beastall in *Steroid Hormones, A Practical Approach* (Green and Leake. eds., IRL Press Limited, 1987). Prior to its release into the bloodstream, the vast majority of newly synthesized DHEA becomes sulfated. The conjugated steroid DHEA-S (shown in FIG. 2), is a secretory product of the adrenal gland in man and certain primates. DHEA-S represents the major steroid hormone in the circulation of humans, and is converted to DHEA via a sulfatase.

Therapeutic uses for DHEA and certain analogs have been reported for diabetes, dry skin, ocular hypertension, obesity, and retroviral infections. Illustrative of these reports are the disclosures of U.S. Pat. No. 4,395,408 (issued Jul. 26, 1983 to Torelli et al.), U.S. Pat. No. 4,518,595 (issued May 21, 1985 to Coleman et al.), U.S. Pat. No. 4,542,129 (issued Sep. 17, 1985 to Orentreich), U.S. Pat. No. 4,617,299 (issued Oct. 14, 1986 to Knepper), U.S. Pat. No. 4,628,052 (issued Dec. 9, 1986 to Peat), U.S. Pat. No. 4,666,898 (issued May 19, 1987 to Coleman et al.), European Patent Application No. 0 133 995 A2 dated Feb. 8, 1984 (inventor, Schwartz et al.), and UK Patent Application No. GB 2 204 237 A dated Apr. 14, 1988 (inventor, Prendergast).

SUMMARY OF THE INVENTION

It is an objective of the invention to provide a method for enhancing the biosynthesis of selected lymphokines by activated T cells. Another objective of the invention is to enhance immune functions in warm blooded animals by restoring their capacity to naturally produce physiological concentrations of these lymphokines with a minimization of side effects. Further objectives of the invention are to provide applications of the method for clinically diagnosing deficiencies of interleukin production, maintaining in vitro tissue cultures of T cells, and overcoming certain types of immunosuppression associated with elevated GCS levels, caused by endogenous production or exogenous administration. Final objectives of the invention are to provide applications of the method as a vaccine adjuvant to selectively direct the vaccine-induced immune response down a protective, rather than a potentially pathologic or non-protective, immunologic pathway, as a treatment for naturally occurring ageing-related decreases in immune function, as a treatment for stress or trauma-induced decreases in immune function, and as a means to facilitate desensitization to agents to which a warm-blooded animal is allergic.

DHEA-S is a prohormone which is naturally converted to DHEA in the peripheral lymph nodes of animals with normal immune function. The DHEA produced then influences the T lymphocytes within the lymph node and exerts controlling influences on their ability to respond when activated. This provides a means to regulate the potential of T cells by fluctuating the degree to which a particular steroid hormone exists within a particular tissue. Old individuals and/or stressed individuals, including humans, lose the capacity to produce DHEA-S, resulting in altered T-cell responsiveness. Various embodiments of the invention restore the metabolite produced from DHEA-S in the anatomic compartment in which T-cell responsiveness is required for normal immune responses to T-cell-dependent antigens.

Accordingly, one aspect of the invention is a method for treating naturally occurring age-related decline in immune function, comprising administering to a warm blooded animal at least one steroid hormone which enhances T cell lymphokine production, wherein the steroid hormone is selected from the group consisting of DHEA and DHEA cogeners.

Another aspect of the invention is a method for treating naturally occurring age-related decline in immune function, comprising administering to a warm blooded animal at least one steroid hormone which enhances T cell lymphokine production, wherein the steroid hormone is a DHEA prohormone.

Yet another aspect of the invention is a method for augmenting in an immunodeficient individual an immune response comprising administering to the individual a pharmaceutical composition comprised of a prohormone of DHEA.

An additional aspect of the invention is a method for augmenting in an immunodeficient individual an immune response comprising administering to the individual DHEA, and wherein the immunodeficiency is due to trauma.

Still another aspect of the invention is a method for augmenting in an immunodeficient individual an immune response to an antigen comprising administering to the individual a steroid selected from DHEA and a DHEA cogener, wherein the administration is such that the DHEA and antigen will drain to the same lymph node.

BRIEF DESCRIPTION OF THE DRAWINGS

FIG. 22A is the dose response curve for DEX of example 18;

FIG. 22B is the dose response curve for Corticosterone of example 18;

FIG. 22C is the dose response curve for 1.25 dihydroxy vitamin D3 (1.25(OH)$_2$D$_3$) of example 18.

DETAILED DESCRIPTION OF THE INVENTION

Figure 1:
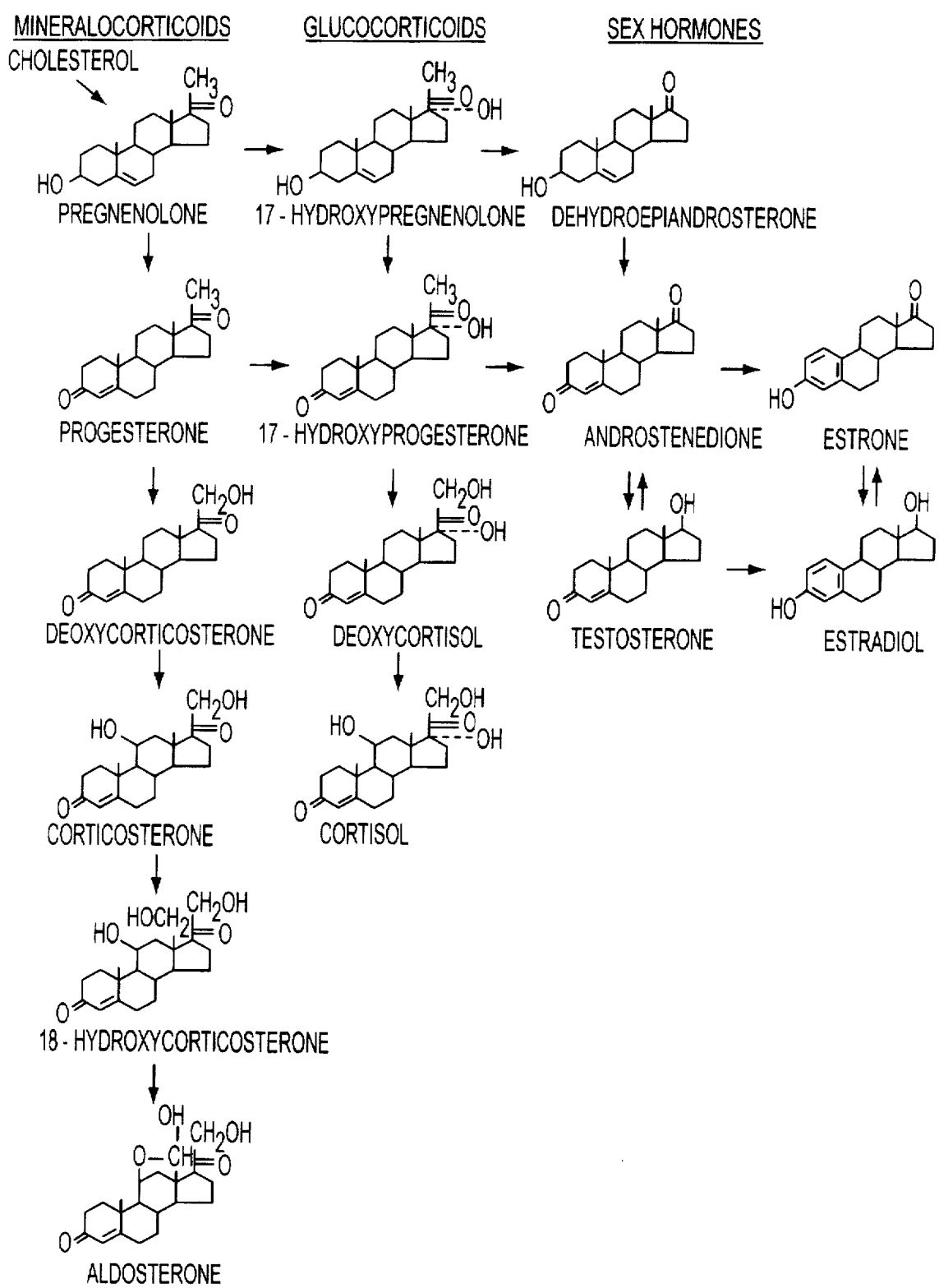
FIG. 1 is a diagram showing the biosynthetic relationship of DHEA to other steroid hormones.
Figure 2:
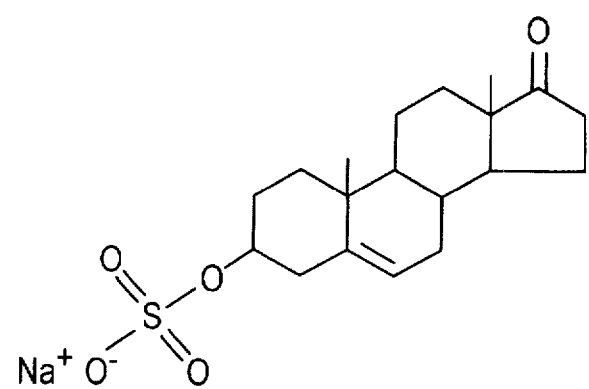
FIG. 2 is a diagram of DHEA-S.

The most important function of the immune system is to provide its host with protection against diseases. To carry out these tasks, a large and diverse array of effector mechanisms have evolved, the majority of which exhibit antigen specificity. Each individual effector mechanism possesses a degree of uniqueness with respect to its ability to influence the rate of progression, to detoxify, or to promote the elimination of microbial pathogens or tumor cells. Such a diversity in available mechanisms is absolutely essential since no single effector response can effectively deal with all forms of pathogenic insults. Furthermore, to protect normal function of the various non-lymphoid organ systems and tissues of the body requires careful selection, activation, and compartmentalization of the most appropriate types of immune effector mechanisms. Equally important is the simultaneous capacity to down-regulate the development of other types of responses. Immunologic effector responses must, therefore, be both effective and practical, and at the same time be appropriately regulated anatomically to reduce the risk of pathologic consequences.

The nonlymphoid tissues and organs of the body, which work collectively to sustain the life of the host, must also be capable of providing regulatory information to cells of the immune system. This information, mediated through the activities of inflammation-induced tissue cytokines, prostaglandins, plus other types of biological response modifiers, becomes integrated into the complex equation to control the mechanisms which regulate effector response selection.

T cells, through their capacity to produce a number of lymphokines in response to activation, play a central role in guiding the development of immune effector responses. Mechanisms which operate to control the synthesis and secretion of these pleiotropic biologic response modifiers, therefore, directly influence the quantitative and qualitative nature of immunity. The lymphokines and cytokines provide important information, not only to cells of the immune system, but also to cells of the other tissue and organ systems. For this information to be meaningful, it is essential that lymphokine production remains tightly controlled at the levels of both cellular source and duration. Autocrine and paracrine effects by lymphokines and cytokines should be the norm, since only a few species of lymphokines and cytokines are capable of working effectively when provided via endocrine routes. These essential anatomic restrictions, therefore, cannot be adequately provided by bolus injection of recombinant lymphokines and/or cytokines, and may explain the limited success associated with this form of therapy.

The vast majority of the T cells in the peripheral circulation are known to reside within the recirculating T cell pool. These cells continuously enter and exit secondary lymphoid organs throughout the body, maintaining residence within any particular site for only finite periods of time. Over the lifespan of any individual mature T cell, therefore, it has probably taken up temporary residence in most of a host's secondary lymphoid organs. T-cell recirculation provides the immune system with a means for clonally-restricted T cells to provide a level of surveillance over all the tissue and organ systems.

It is universally accepted that most T cells acquire their specificity for antigen, and a self-MHC-restricting element, during processes which occur during their ontogeny within the thymus. However, the extent to which intrathymic maturation confers genetic restrictions upon individual T cells that regulate their potential for immunologic involvement has not been delineated.

A general concept which explains the results in the Examples, but which is not intended to limit our invention, is that the genetic programs of resting recirculating T cells are continuously being altered by extrinsic environmental influences. The steroid hormones, either presented in their active forms systemically (e.g. glucocorticosteroids (GCS)), or being provided to T cells only within discrete microenvironments as a consequence of end-organ metabolism [e.g., DHEA, DHT, OR 1.25(OH)$_2$D$_3$] perform important roles in this process. The basal regulation of the immune system at the level of the T cell requires the continual presence of the needed substrates (prohormones). The anatomic compartmentalization of functional potential for T cells, therefore, would be dependent on the cellular source of the steroid metabolizing enzymes able to convert the steroid hormone substrates to their bioactive species. Our studies show that macrophages can contain each of these enzymes.

More specifically, DHEA-S is naturally converted to DHEA in the peripheral lymph nodes of animals with normal immune function. The DHEA produced then influences the T lymphocytes within the lymph node and exerts controlling influences on their ability to respond when activated. This provides a means to regulate the potential of T cells by fluctuating the degree to which a particular steroid hormone exists within a particular tissue. Old individuals and/or stressed individuals, including humans, lose the capacity to produce DHEA-S, resulting in altered T-cell responsiveness. The invention in its various embodiments restores the metabolite produced from DHEA-S in the anatomic compartment in which T-cell responsiveness is required for normal immune responses to T-cell-dependent antigens.

As used herein, the term "individual" refers to a vertebrate and preferably to a member of a species which exhibits DHEA-S sulfatase activity, and includes but is not limited to domestic animals, sports animals, and primates, including humans.

The term "effective amount" refers to an amount of DHEA-S, DHEA, or DHEA cogener sufficient to restore normal immune responsiveness in an immunodeficient subject to which it is administered, i.e., it restores DHEA in the anatomic compartment in which T-cell responsiveness is required to a level for normal immune responses to T-cell-dependent antigens. The exact amount necessary will vary from subject to subject, depending on the species, age, and general condition of the subject, the severity of the condition being treated, the mode of administration, etc. Thus, it is not possible to specify an exact effective amount. However, the appropriate effective amount may be determined by one of ordinary skill in the art using only routine experimentation.

As used herein, the term "immunodeficient individual" means an individual whose response to immune stimulation to a foreign antigen is significantly less than that of the average of normal individuals of the same species. Methods of determining "immunodeficiency" are known in the art, and include, for example, an examination of lymphokine production by activated T cells; the ability of the individual to demonstrate contact hypersensitivity; the ability of the individual to raise a humoral response to antigen challenge, or the resistance of the individual to infection by microorganisms.

"Treatment" refers to the administration of a composition to an individual which yields a protective immune response, and includes prophylaxis and/or therapy.

An "antigen" refers to a molecule containing one or more epitopes that will stimulate a host's immune system to make a secretory, humoral and/or cellular antigen-specific response. The term is also used inter-changeably with "immunogen".

An "immunological response" to a composition or vaccine comprised of an antigen is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By "vaccine composition" or "vaccine" is meant an agent used to stimulate the immune system of an individual so that current harm is alleviated, or protection against future harm is provided.

"Immunization" refers to the process of inducing a continuing high level of antibody and/or cellular immune response which is directed against an antigen to which the organism has been previously exposed.

As used herein, the term "prohormone" pertains to water soluble precursors of DHEA, i.e., DHEA derivatives from which DHEA may be synthesized in vivo, for example, DHEA-S (and other precursors known in the art).

As used herein, a "pharmacologic dose" is one which gives a desired physiological effect.

The practice of the present invention will employ, unless otherwise indicated, conventional techniques of molecular biology, microbiology, biochemistry, and immunology, which are within the skill of the art. Such techniques are explained fully in the literature. See, e.g., ANIMAL CELL CULTURE (R. I. Freshney ed. 1986); IMMOBILIZED CELLS AND ENZYMES (IRL Press, 1986; the series, METHODS IN ENZYMOLOGY (Academic Press, Inc.), IMMUNOCHEMICAL METHODS IN CELL AND MOLECULAR BIOLOGY (Academic Press, London), Scopes, (1987); and HANDBOOK OF EXPERIMENTAL IMMUNOLOGY, Volumes I–IV, (D. M. Weir and C. C. Blackwell, eds., 1986.) All patents, patent applications, and publications mentioned herein, both supra and infra, are hereby incorporated herein by reference.

One embodiment of the invention is a method for enhancing or maximizing the production of T cell lymphokines which are correlated with protective immunity. The method comprises exposing T cell lymphocytes which have a potential to make selected T cell lymphokines to appropriate concentrations of particular steroid hormones prior to activation. If the exposure is in vitro, the particular steroid hormone to which the T cell lymphocyte is exposed depends upon the lymphokine which is selected for enhancement or maximized production. If the exposure is in vivo, a pharmaceutical composition comprised of the. steroid hormone is administered to the individual, particularly to an immunodeficient individual. Immunodeficiency may be for a variety of reasons, for example, age, i.e., very young (e.g., neonate) or aged, stress, or trauma. The administration to the individual is by techniques known in the art, including, for example, parenteral, transdermal, or transmucosal.

In accordance with the invention, exposing T cell lymphocytes which have a potential to make selected T cell lymphokines to DHEA or a DHEA cogener prior to activation enhances the production of IL-2, IL-3, γ-IFN, and GM-CSF. DHEA cogeners which are useful in the invention have the following structure:

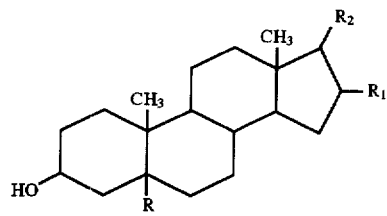

in which R is hydrogen in alpha or beta configuration or nothing, resulting in a double bond between carbon atoms 5 and 6; $R_1$ is hydrogen or a halogen in α-configuration; and R2 is oxygen or methyl ketone (—$COCH_3$); or

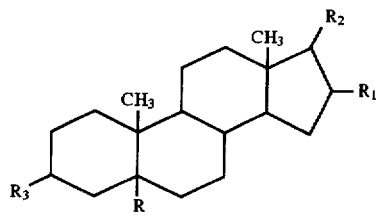

in which R is hydrogen in alpha or beta configuration or nothing, resulting in a double bond between carbon atoms 5 and 6; $R_1$ is hydrogen or a halogen in α-configuration; R2 is oxygen or methyl ketone (—$COCH_3$); and $R_3$ is OH or sulfate.

Alternatively, and particularly in vivo, the selected steroid hormones may be administered to individuals through precursor substances which are then metabolized to DHEA or its metabolites. For example, the sulfonated form of DHEA, DHEA-S, can be administered provided that the administration is to an individual that can metabolize the prohormone to DHEA by tissue-associated DHEA-sulfatases.

The simultaneous enhancement or maximization of the production of more than one T cell lymphokine may be achieved by exposing the T cell lymphocyte to more than one steroid hormone prior to activation. The exposure to more than one steroid hormone can be simultaneous or sequential. The concentration of each of the steroid hormones should be balanced to achieve the desired enhancing effects. For example, if it were desirous to enhance the production of IL-2, γ-IFN, and IL-4, the T cell lymphocytes could be exposed to physiologic or pharmacologic levels of DHEA and a physiologic level of GCS. This would avoid the IL-2 and γ-IFN depression which is characteristic of a pharmacologic level of GCS.

Evidence derived from experimental and clinical observations indicates that immunologic reactions elicited to either simple or complex antigens often manifest as a balanced heterogenous blend of both cellular and humoral components, with the fractional contribution of any individual type of effector mechanism oftentimes dominating the overall response. This level of heterogeneity is essential to the development of a protective immune response. Alterations to this natural balance, whether caused by genetic or physiologic changes associated with age or stress or trauma, can lead to a depressed capacity to elicit protective immune responses, and might also lead to immunologic responses having pathologic consequences.

Administration of steroid hormones, particularly DHEA-S or DHEA or DHEA-cogeners in accordance with the invention would be useful in treating such immune system imbalances in individuals. For example, immunosuppression (a form of immunodeficiency) in warm blooded animals may be mediated by elevated GCS levels. These elevated levels can result from a variety of causes including, but not limited to, stress and trauma (including, for example, post-surgical trauma, burn trauma), as a secondary consequence to any clinical condition which causes an elevated production of IL-1, or therapeutic treatment for a variety of clinical conditions. The elevated GCS levels can result in an imbalance in the production of essential interleukins. The normal balance of essential interleukin production may be restored by therapeutic administration of DHEA, DHEA-S, or its cogeners.

Additionally, if it were known that elevated GCS levels were the result of certain behavior or maladies, administration of DHEA-S, DHEA, or DHEA cogeners could be used as a prophylaxis prior to the onset of the elevation in GCS levels and resultant immunosuppression. In these cases, where the administration is chronic, it is advisable to use the prohormone form (e.g., DHEA-S) to prevent side effects associated with the administration of large doses of DHEA. For instance, there is a bovine malady commonly known as "Shipping Fever" which has a high rate of morbidity and mortality associated with the stress induced by long distance shipment. This stress is associated with chronic increased levels of GCS. Prophylactic administration of prohormones (e.g., DHEA-S) in accordance with the invention prior to and/or during bovine shipment may counteract the immunosuppressive effects of the chronically elevated GCS levels, reducing the risk of these animals to infectious agents and weight loss.

The invention may also be used as a diagnostic tool in evaluating lymphokine production deficiency. In this application T cell lymphokine production of a first group of T-cell lymphocytes which have a potential to make selected T cell lymphokines after T cell lymphocyte activation is measured. A second group of the same type of T cell lymphocytes is exposed to a particular steroid hormone prior to T cell activation. The selected T cell lymphokine is then measured after activation. The amount of T cell lymphokine production of the two groups of T cell lymphokines are compared. The sensitivity of the diagnostic tool is maximized when the amount of the particular steroid hormone to which the second group of T cell lymphocytes is exposed is sufficient to maximize the production of the T cell lymphokines which the particular steroid hormone enhances. For example, if the T cell lymphokine is IL-2, or IL-3, or γ-IFN, or GM-CSF, the preferred steroid hormone may be selected from the group DHEA or a DHEA cogener having the structure recited above.

Another application of the invention is to treat naturally occurring age-related decreases in immune function, which correlate with a decrease in circulating DHEA-S levels. Associated with age related decline in immune function is a decrease in the production of certain lymphokines. Treatment of aging, warm blooded animals with steroid hormones, preferably DHEA-S or DHEA-cogeners, substantially restores the production of the selected lymphokines involved in the cascade leading to immunologic competence.

Generally, the person in charge of the administration of the steroids, DHEA, DHEA-S, or DHEA-cogeners will choose the appropriate form of the steroid based upon the compartmentalization effect and metabolic products resulting therefrom. For example, if the indication for administration is prophylaxis or chronic therapeutic treatment, the prohormone DHEA-S is preferred to escape the side effects associated with of the administration of chronic high levels of DHEA. In this case the level of DHEA-S may be in the range of about 5 to about 100 mg per day, preferably may be in the range of about 10 to about 80 mg per day, and even more preferably may be in the range of about 15 to about 60 mg per day.

Alternatively, if the indication for treatment is acute trauma or stress, it may be preferable to treat with a bolus administration of DHEA. The bolus administration may be in the range of about 1 to about 20 mg per kg of body weight, more usually may be in the range of about 2 to about 10 mg per kg of body weight, and preferably may be in the range of about 3 to about 8 mg per kg of body weight.

The compounds of the present invention can be administered to the immunologically deficient individual in a variety of forms adapted to the chosen route of administration, for example, orally, intravenously, intramuscularly, or via subcutaneous, topical, or inhalation routes.

Pharmaceutical compositions made up of formulations comprised of the steroids (particularly DHEA, DHEA-S, and DHEA-cogeners) and suitable for the administration by each of these routes may be prepared by one of ordinary skill in the art. See, for example, Remington's Pharmaceutical Sciences, 17th Edition (1985, Mack Publishing Company, Easton, Pa.). For example, the pharmaceutical composition containing the steroid may also contain a carrier or solid or be encapsulated in a material that is non-toxic to the inoculated animal and is compatible with the steroid. Suitable pharmaceutical carriers include liquid carriers, such as normal saline and other non-toxic salts at or near physiological concentrations, and solid carriers not used for humans, such as talc or sucrose, also feed for farm animals. When used for administering via the bronchial tubes, the steroid hormone is preferably presented in the form of an aerosol.

Another application of the invention is to use a pharmaceutical composition containing the steroid, preferably DHEA or a DHEA cogener, as a vaccine adjuvant to augment or selectively direct the vaccine-induced immune response down a protective immunologic pathway. When the individuals are immunized with an immunizing agent, administration of the steroid may be prior to or contemporaneously with the vaccination. Typical methods of administering the steroid hormone include implants, mixing the steroid hormone with the immunizing agent, or topically applying the steroid hormone composition to skin sites which drain to the same lymph nodes as the antigen of the vaccine. This latter method is preferably used with individuals who are immunologically deficient due to low levels of DHEA-S and/or DHEA and in whom one wishes to augment the immune response, for example, the aged or neonates or individuals who are therapeutically immunosuppressed.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLES

Example 1

DHEA Enhances IL-2 Production by Activated Murine T Cells

Figure 3A:
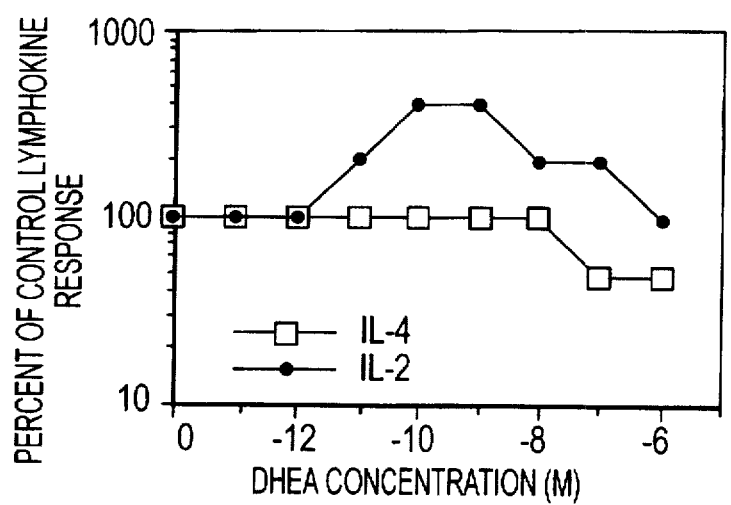
FIG. 3A is a graph showing the dose response curve for DHEA on the production of IL-2 and IL-4 by activated murine T cells.
Figure 3B:
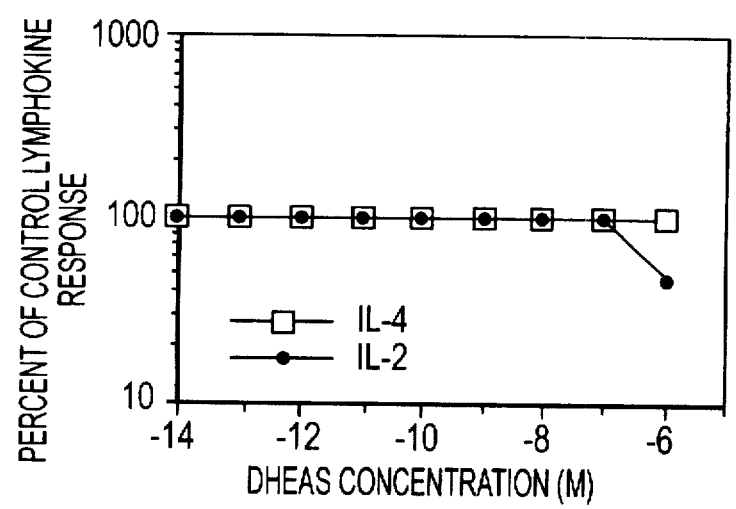
FIG. 3B is a graph showing the dose response curve for DHEA-S on the production of IL-2 and IL-4 by activated murine T cells.

In this experiment the capacity of DHEA and DHEA-S to alter the production of IL-2 and IL-4 following in vitro lymphocyte treatment or exposure was evaluated. DHEA significantly enhanced the production of IL-2 over a wide dose range, and DHEA-S, over the same dose range, had no effect on IL-2 and IL-4 production. FIG. 3A is the dose response curve of DHEA and FIG. 3B is the dose response curve of DHEA-S developed in this experiment.

Spleen cells obtained from normal BALB/c mice were prepared as a single cell suspension at a concentration of $1 \times 10^7$ cells/ml in RPMI 1640 supplemented with 2 mM L-glutamine, $5 \times 10^{-5}$M 2-mercaptoethanol, 20 μg/ml gentamycin-sulfate, and 1% Nutridoma-NS (Boehringer-Mannheim). Individual aliquots of cells were then pulsed for 30 minutes at 37° C. with the indicated concentrations of DHEA or DHEA-S. After pulsing, the cells were washed several times in balanced salt solution, resuspended in fresh medium, and then dispensed into 24-well culture plates with a stimulatory concentration of anti-CD3 (Leo et al. (1987), Proc. Natl. Acad. Sci. USA 84:1374). After a 24-hour incubation period, culture supernatants were harvested for assessment of IL-2 and IL-4 activity using the method of Mossman (J. Immunol. Meth. (1983)). In this experiment, 100% control titers of IL-2 and IL-4 from normal stimulated splenocytes in FIG. 3A were 640 and 160 units/ml, respectively. For control splenocytes from FIG. 3B, 100% control titers of IL-2 and IL-4 were 2560 and 320 units/ml, respectively.

This same experiment was repeated to assay for γ-IFN production. A dose response curve similar to that reported in FIG. 3A for DHEA was obtained for γ-IFN.

This same experiment was performed using the DHEA cogener 16-alpha-bromo DHEA in place of DHEA. A dose response curve similar to that reported in FIG. 3A was obtained for 16-alpha-bromo DHEA.

Example 2

DHEA Enhances IL-2 Production in GCS-Treated Normal Splenocytes and Cloned T Cell Lines The capacity of DHEA to facilitate a reversal of glucocorticoid-induced suppression of IL-2 production by either normal murine lymphocytes, or cloned T cell lines with similarities to either Th1-type or Th2-type helper T cells was evaluated.

Figure 4A:
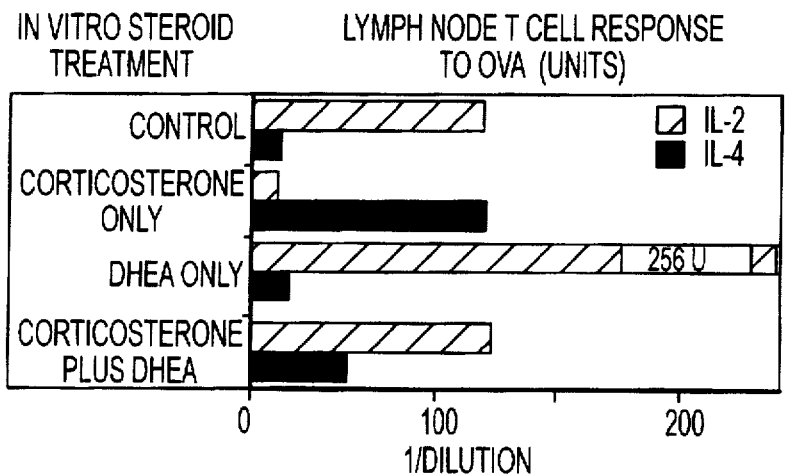
FIG. 4A is a graph showing the effect of corticosterone and/or DHEA on the in vitro lymph node T cell response to OVA.
Figure 4B:
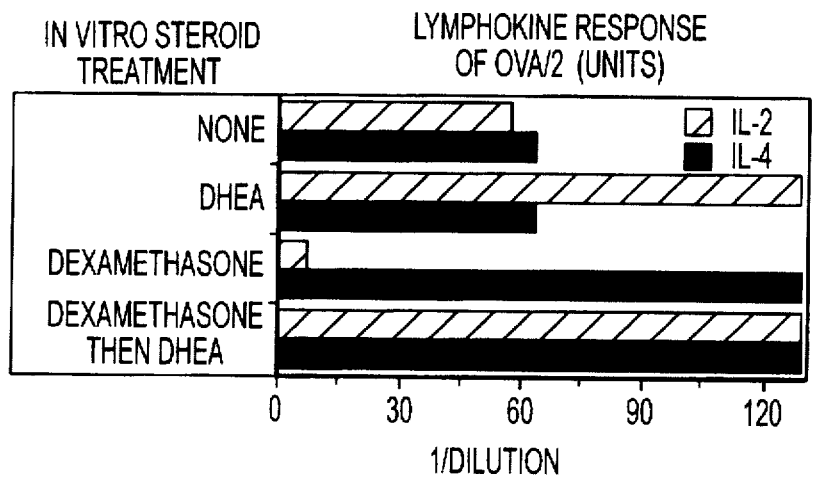
FIG. 4B is a graph showing the effect of dexamethasone (DEX) and/or DHEA on the in vitro lymphokine response of OVA/2, an ovalbumin-specific cloned T cell line.
Figure 4C:
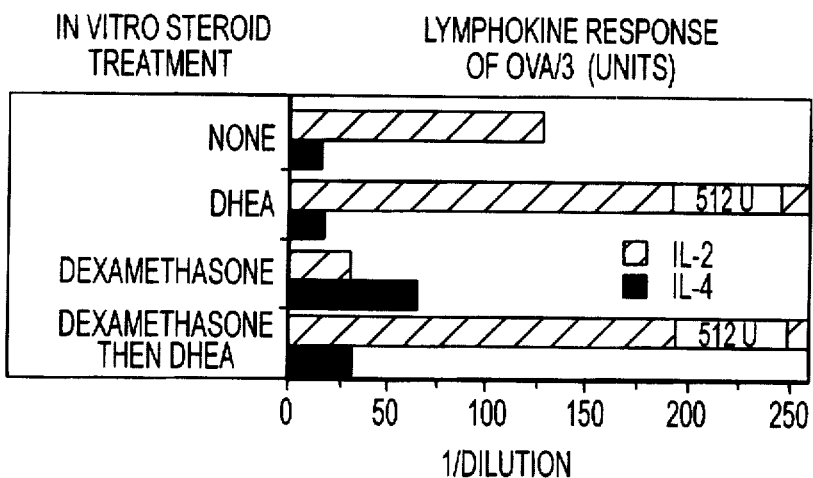
FIG. 4C is a graph showing the effect of dexamethasone (DEX) and/or DHEA on the in vitro lymphokine response of OVA/3, an ovalbumin-specific cloned T cell line.

Single cell suspensions of normal murine spleen cells were prepared in Nutridoma-supplemented complete RPMI at $10^7$ cells/ml. They were then pulsed with $10^{-7}$M corticosterone and/or $10^{-8}$M DHEA as described in FIG. 4A. After several washes, the cells were stimulated with anti-CD3. The enhancement of IL-2 production by DHEA exposed normal splenocytes is shown in FIG. 4A. FIG. 4B and FIG. 4C show the regulation of lymphokine production by two ovalbumin (OVA)-specific cloned T cell lines. The OVA-specific T cell clones were derived from nylon-wool enriched splenic T cells from OVA-immunized (C3H×C57/B6) F$_1$ mice using the method of Berzofsky (1985), J. Immunol. 35:2628. OVA/3 and OVA/2 cell lines were derived from different clonings, each having distinct patterns of lymphokine production. Culture conditions and assay procedures for IL-2 and IL-4 are as in Example 1.

Referring to FIG. 4A, exposure of splenocytes to the effects of corticosterone ($10^{-7}$M) greatly reduced the capacity of cells to produce IL-2 subsequent to activation with anti-CD3. DHEA treatment alone augmented IL-2 production. Lymphocytes exposed to corticosterone and DHEA, followed by their activation in vitro, produced normal or enhanced levels of IL-2 and enhanced levels of IL-4.

Referring to FIG. 4B and FIG. 4C, OVA/2 [an ovalbumin (OVA)-specific cloned T cell line with characteristics similar to Th2-type cells) and OVA/3 (a cloned T cell line with characteristics similar to Th1-type cells), were exposed in vitro to the effects of DHEA and/or glucocorticoids prior to their culture with antigen and syngeneic antigen-presenting cells. As shown in FIG. 4C, DHEA treatment of OVA/3 greatly augmented the capacity of this cell line to produce IL-2, while exposure to DEX resulted in an IL-4 dominant phenotype, similar to what is observed with Th2-type clones. Treatment of OVA/3 with DEX followed by DHEA, resulted in a marked elevation in IL-2 production with only a minimal enhancement of IL-4. As shown in FIG. 4B, the effects of steroid treatment on the capacity of OVA/2 to produce TCGF gave comparable results. DHEA exposure of this T cell clone was capable of shifting the pattern of TCGF production from a Th2-like to a Th1-like phenotype (IL-2 dominant), while DEX treatment alone augmented IL-4 production following activation in vitro with OVA. Treatment of OVA/2 with both DEX and DHEA caused an enhanced capacity to produce both IL-2 and IL-4.

Example 3

A Single Injection of Mice with DHEA or DHEAS Enhanced the Biosynthesis of IL-2 by Activated Lymphoid Cells This example demonstrates the effects of in vivo administration of DHEA and DHEA-S on IL-2 and IL-4 biosynthesis.

Figure 5:
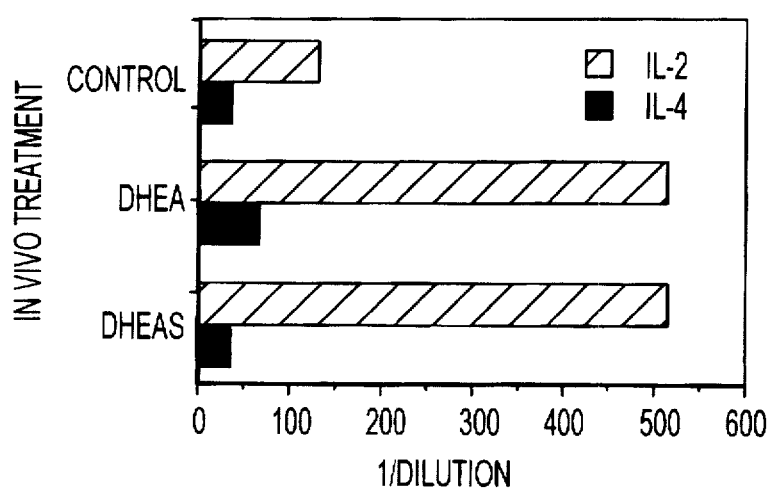
FIG. 5 is a graph showing the results of the effect of DHEA and DHEA-S in vivo on IL-2 and IL-4 production by spleen cells.

Groups of (C3H×BL/6)F1 mice were given a single intraperitoneal injection of 100 μg DHEA or DHEA-S. After three days, spleen cells from the treated groups, plus spleen cells from an untreated age-matched control group, were prepared for culture as described in Example 1. The relative titers of IL-2 and IL-4 in the 24-hour culture supernatants were determined in the presence of anti-IL-2, or anti-IL-4, or both anti-IL-2 and anti-IL-4, or no blocking antibodies. The assay was read visually. FIG. 5 presents the results of the study. Non-activated cultured lymphoid cells produced undetectable (less than 2 units) of either IL-2 or IL-4.

Example 4

DHEA Enhances IL-2 Production in Splenocytes from Corticosterone-Treated Mice The reversal of the inhibitory effects caused by chronic glucocorticoid administration to normal mice in vivo on the capacity of their T cells to produce IL-2 was demonstrated as follows.

Figure 6:
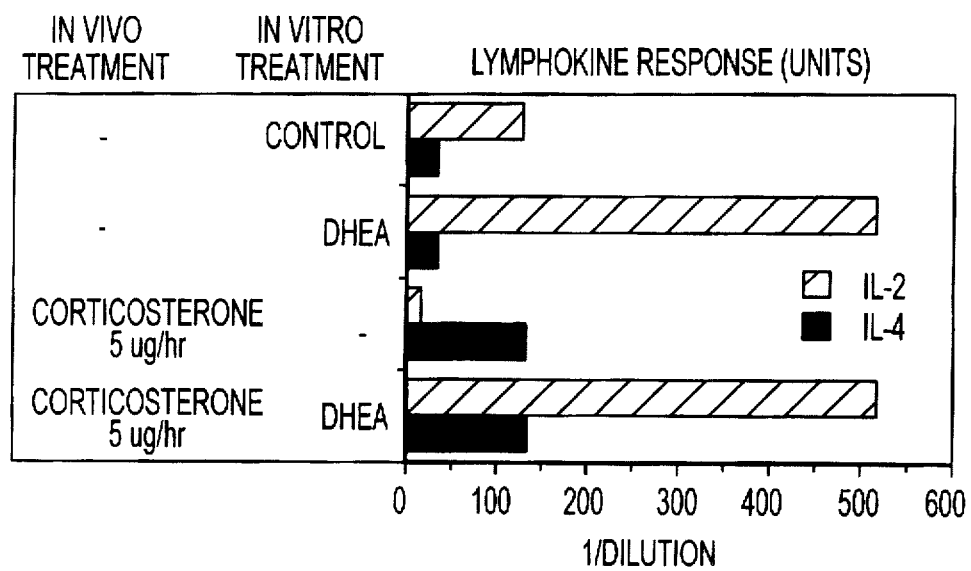
FIG. 6 is a graph showing the results of a pulse of DHEA in vitro on IL-2 and IL-4 production by splenocytes from mice treated with corticosterone in vivo.

Biodegradable pellets (Innovative Research, Inc.) containing corticosterone and designed to deliver the steroid at a dose of 5 μg/hr were implanted subcutaneously into (C3H×BL/6) F$_1$ mice. The splenocytes from the mice were harvested 72 hours after the implantation. Prior to activation, the splenocytes were pulsed with a short pulse of DHEA ($10^{-8}$M). Culture and assay procedures for IL-2 and IL-4 were as described in Example 1. The results are presented in FIG. 6.

As seen in the figure, the DHEA pulse caused a significant enhancement of IL-2 production. Under these conditions, the glucocorticoid-induced augmentation in IL-4 synthesis was not affected, resulting in a population of lymphoid cells capable of producing high levels of both IL-2 and IL-4.

Example 5

DHEA in vivo Enhances IL-2 Production in Mice with and without Corticosterone Treatment This example demonstrates that DHEA administered in vivo influences the profile of T cell growth factors (TCGF) produced by splenocytes isolated from treated animals.

Biodegradable pellets (Innovative Research, Inc.) containing corticosterone or DHEA that deliver the steroids at 5 µg/hr were implanted subcutaneously into three separate groups of BALB/c mice 72 hours prior to harvesting and preparation of spleen cells. Single cell preparations of splenocytes from each group were cultured as described in Example 1, and stimulated with the polyclonal T cell mitogen, anti-CD3. After 24 hours, culture supernatants were collected and assayed for IL-2 and IL-4 activity as described in Example 1.

Figure 7:
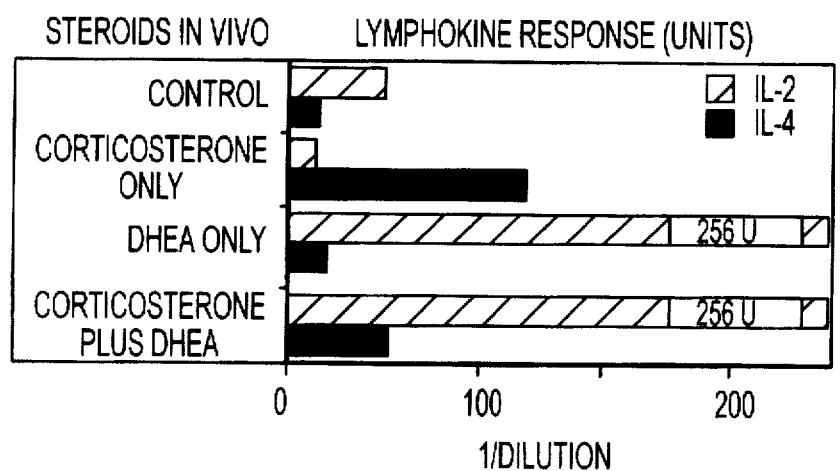
FIG. 7 is a graph showing the results of DHEA and/or corticosterone administered in vivo on the levels of IL-2 and IL-4 production by activated splenocytes.

As seen in FIG. 7, the stimulation of splenocytes isolated from normal animals consistently gave a standard pattern of TCGF production where IL-2 dominated over IL-4. Lymphocytes isolated from corticosterone-treated animals demonstrated a marked reversal of this pattern; IL-4 consistently represented the dominant TCGF. Similar to what is observed following an in vitro treatment with this androgen steroid, activated splenocytes from the DHEA-treated animals exhibited an enhancement in IL-2 production. Under conditions where both steroids were elevated in vivo, it was found that isolated splenocytes from these animals produced enhanced levels of both IL-2 and IL-4 subsequent to their activation with anti-CD3 in vitro.

Example 6

Figure 8:
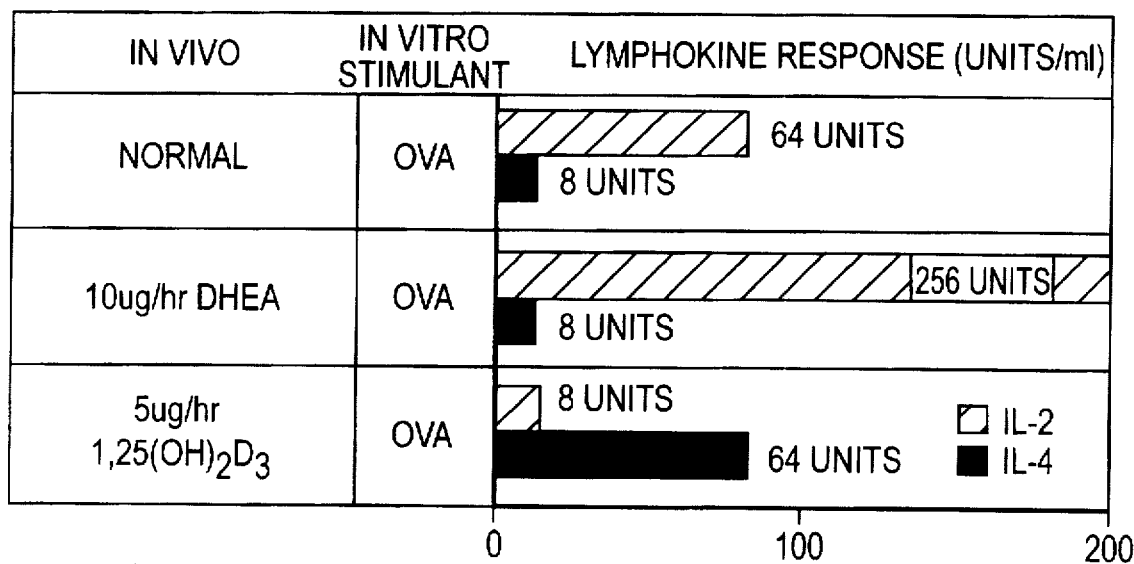
FIG. 8 is a graph showing the effect of DHEA and 1.25(OH)$_2$D$_3$ administered in vivo on lymphokine production by activated splenocytes.

The Effect of DHEA and 1,25-dihydroxyvitamin D3 in vivo on IL-2 and IL-4 Production in vitro CH3 mice received implants of biodegradable DHEA or 1,25(OH)$_2$D$_3$ pellets designed to deliver steroid at a rate of 5 and 1.25 µg/hr, respectively. Three days after implantation, both the steroid treated groups and a normal control group of mice were immunized in the hind footpads with 100 µg OVA in CFA. Ten days after immunization, the draining lymph nodes and spleens from all groups were prepared for culture. Lymph node cells were stimulated with 100 µg OVA. Culture supernatants were assayed for IL-2 and IL-4 activity after 24 hours using the HT-2 bioassay. The results are shown in FIG. 8. From the figure it may be seen that DHEA administration caused approximately a four-fold increase in IL-2 production, and no stimulation of IL-4 production. In contrast, 1,25(OH)$_2$D$_3$ administration caused an approximate eight-fold increase in IL-4 production, but did not stimulate IL-2 production.

Similar alterations in the ability of antigen-activated T cells to produce IL-2 and IL-4 were observed when the steroid hormone was mixed with the immunizing antigen, or was topically applied to skin sites above the site of vaccination.

Example 7

The Reversal of Age-related Decline in IL-2 and γ-IFN Production

This example demonstrates age-related decline in the production of certain lymphokines, and restoration by steroid hormone treatment. The lymphokines assayed are IL-2, IL-4, and γ-IFN; the steroid hormone administered is DHEA.

Figure 9:
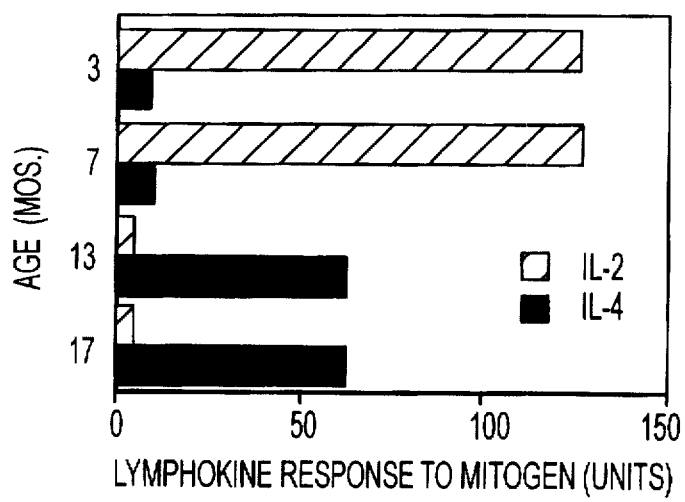
FIG. 9 is a graph showing age-associated changes in lymphokine production by activated splenocytes.

Age associated changes in lymphokine production are shown in FIG. 9. (CH3×BL/6)F$_1$ mice of the indicated ages were sacrificed and their spleen cells prepared for culture with mitogen; anti-CD3. Culture supernatants were harvested and evaluated for the relative contribution of IL-2 and IL-4 using the HT-2 bioassay. As seen in the figure, aged mice (13 and 17 months) produced significantly less IL-2 and significantly more IL-4 than did younger mature mice (3 and 7 months). Non-activated cells produced less than 1 unit of either IL-2 or IL-4.

Figure 10:
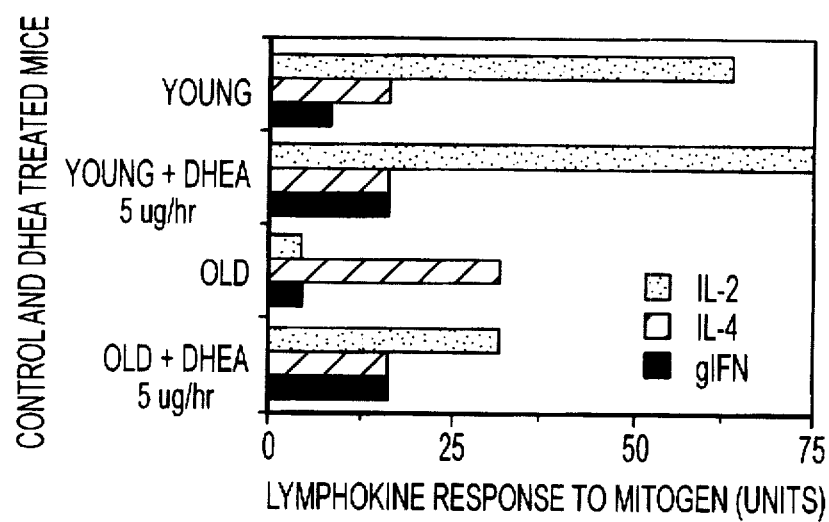
FIG. 10 is a graph showing the effect of DHEA administered in vivo on lymphokine production in splenocytes isolated from aged and mature young mice.
Figure 11A:
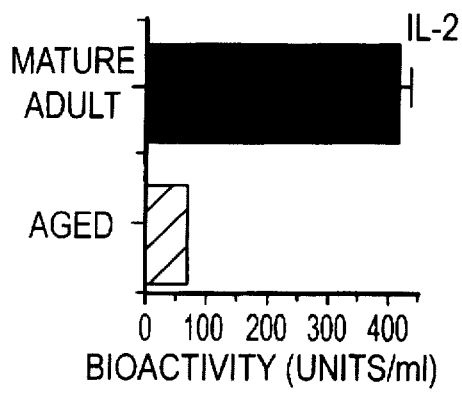
FIG. 11A is a graph showing the pattern of IL-2 produced by T cells from aged BALB/c donor mice and younger donor mice.
Figure 11B:
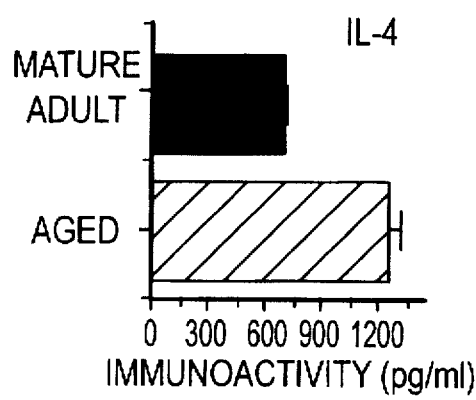
FIG. 11B is a graph showing the pattern of IL-4 produced by T cells from aged BALB/c donor mice and younger donor mice.
Figure 11C:
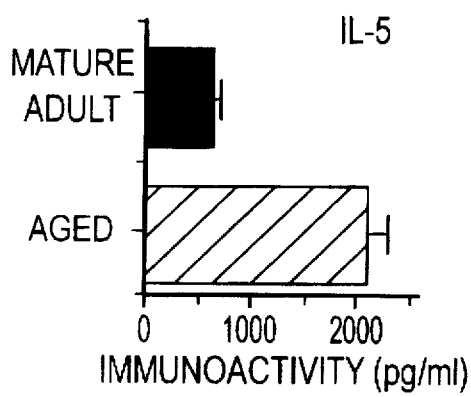
FIG. 11C is a graph showing the pattern of IL-5 produced by T cells from aged BALB/c donor mice and younger donor mice.
Figure 11D:
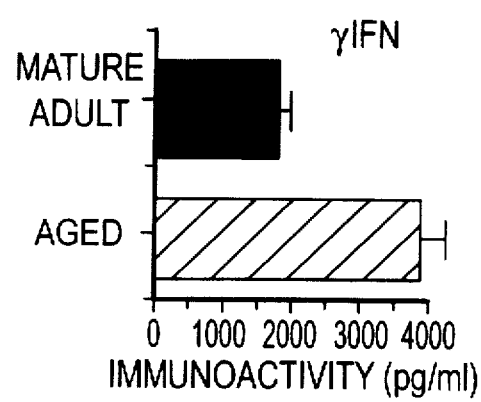
FIG. 11D is a graph showing the pattern of γ-IFN produced by T cells from aged BALB/c donor mice and younger donor mice.
Figure 11E:
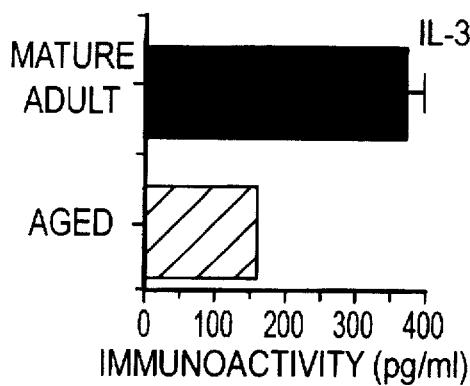
FIG. 11E is a graph showing the pattern of IL-3 produced by T cells from aged BALB/c donor mice and younger donor mice.
Figure 11F:
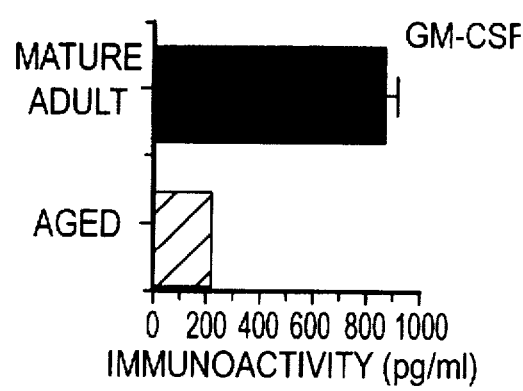
FIG. 11F is a graph showing the pattern of GM-CSF produced by T cells from aged BALB/c donor mice and younger donor mice.

A reversal of the aging effect on IL-2 production by DHEA is shown in FIG. 10. In the study, both young (6 mos.) and old (16 mos.) mice were implanted with DHEA pellets delivering a dose of 5 µg/hr. After three days, DHEA groups and control age-matched groups were sacrificed and their spleen cells prepared for culture with the mitogen anti-CD3. Culture supernatants were harvested and evaluated for the relative contribution of IL-2 and IL-4 using the HT-2 bioassay, and for γ-IFN using the assay of Green. Non-activated cells produce less than 1 unit of either IL-2 or IL-4 and no detectable γ-IFN.

Similar enhancement in the capacity of lymphocytes derived from old mice to produce IL-2 was observed following a direct exposure of the splenocytes in vitro to DHEA ($10^{-9}$ to $10^{-7}$M).

Example 8

Activated T cells from Aged donors Produce an Altered Pattern of Lymphokines Compared to Normal Using a serum-free culture system which allows in vitro activation of lymphocytes under conditions devoid of the restrictive regulatory influences by platelet-derived growth factor and other serum-associated modulators of cellular activity, lymphocytes from mature adult and aged mice were compared for lymphokine production following T-cell activation. Splenocyte cultures were either stimulated with 1 µg/ml anti-CD3ε or left unstimulated to control for any spontaneous lymphokine production. After a 24-hour incubation period, cell-free culture supernatants were analyzed for lymphokine content. The materials and methods used in these studies were as follows.

The BALB/c mice used were bred from breeding stock originally purchased from the National Cancer Institute. The source of aged mice for these experiments was retired breeders from our own colony. Age and sex-matched mice, ranging in age from 13 to 39 weeks for mature adult, and 112–120 weeks for aged mice were used.

Monoclonal antibody reagents were prepared from culture supernatants of B-cell hybridomas adapted to growth under serum-free conditions. The hybridoma clones secreting rat anti-murine γ-IFN (XMG1.2), AND RAT ANTI-MURINEil-5 (TRFK4 and TRFK5) were obtained from DNAX (Palo Alto, Calif.). The hybridoma clone producing hamster anti-murine CD3ε monoclonal antibody, 1452C-11.2, was obtained from J. Bluestore (University of Chicago), the hybridoma producing antibody specific for murine IL-4 (11B11) and murine γ-IFN (R46A2) was purchased from the ATCC. A number of purified rat anti-murine cytokine antibodies were purchased from PharMingen (San Diego, Calif.) and used for quantitation of specific murine cytokines by capture ELISA; these were anti- murine IL-3 antibodies (cat. nos 18011D and 18022D), biotinylated anti-IL-4 (cat. no. 18042D), anti-murine GM-CSF antibodies (cat. nos. 18091D and 18102D).

Murine recombinant γ-IFN was obtained from Genentech (5×10$^6$ units/mg protein) and used as a reference in the γ-IFN bioassays. Murine recombinant IL-2, IL-4 and IL-5, were derived from culture supernatants of X63Ag8-653 cells transfected with multiple copies of a single murine interleukin gene. After the relative concentration of each lymphokine in culture was determined by a comparison to a known recombinant standard, these reagents were used as reference lymphokines in both bioassays and capture ELISA. Other sources of purified, murine, reference lymphokines were IL-5 obtained as a gift from R. Coffman, DNAX, or IL-2 and IL-4 purchased from Collaborative Research Inc. (Bedford, Mass.). Ovalbumin (Sigma Chemicals, St. Louis, Mo.) was dissolved in double distilled water at a concentration of 20 mg/ml. The solution was filter sterilized and frozen in 3 ml aliquots at −20° C. For immunization, ovalbumin was mixed with the commercial aluminum hydroxide preparation (Maalox), one hundred µg in 25 microliters Maalox was injected into a single hind footpad.

Single cell suspensions of lymphoid cells were prepared from appropriate lymphoid organs of normal mice, washed twice in sterile balanced salt solution and cultured at a density of $1 \times 10^7$ cell/ml/well with a T-cell specific mitogen, routinely anti-CD3ε, in a 24-well Cluster culture plate (Costar, Cambridge, Mass.) for a period of 24 hours to elicit lymphokine secretion. Cell-free culture supernatants were collected and stored at −20° C. until assayed for lymphokine content. The culture period, cell concentrations, and culture medium, consisting of RPMI 1640 supplemented with 1% Nutridoma-SR (Boehringer-Mannheim), antibiotics, 200 mM L-glutamine and $5 \times 10^{-5}$M 2-mercaptoethanol, were all carefully evaluated to determine the optimal conditions for stimulating production of the lymphokines under evaluation.

HT-2 cells were used as an indicator cell line for the bioassay of IL-2, using a modification of a calorimetric assay for cell viability. Each test supernatant is titrated in duplicate in Nutridoma-SR-supplemented media (referred to as serum-free) containing $4 \times 10^3$ HT-2, and saturating amounts of anti-IL-4 monoclonal antibody. During the final 4 hours of a 24-hour incubation, 5 µg of 3-[4,5-Dimethylthiazole-2-yl]-2,5 diphenyl tetrazolium bromide (MTT) is added to each culture, followed by the addition of 100 microliters of a 20% SDS/50% dimethylformamide solution to dissolve formazan crystals. Spectrophotometric readings are recorded at 570 nm–650 nm. One unit of activity in a test supernatant is equivalent to the O.D. of a half-maximal response of HT-2, relative to a standard recombinant source.

Where indicated, the amount of other cytokines in test supernatants was quantitated by capture ELISA, adapted from the method of Schumacher. Briefly,100 microliters of 2 µg/ml capture antibody in 0.05M Tris-HCV (pH9.6) was adsorbed to the wells of a 96-well microtest plate, washed and blocked with PBS/1% BSA. Test supernatants and 2-fold serial dilutions of the appropriate reference cytokine (100 microliters/well) were dispensed and after sufficient incubation and washing, 100 microliters of biotinylated-detection antibody, 1 µg/ml, was dispensed into each well. The ELISA was developed using avidin-HRP and ABTS-substrate. Spectrophotometric readings were recorded at 405 nM. The limit of detection for most of these cytokines is 15–30 pg/ml.

Anti-Ovalbumin antibody ELISA was performed as follows. Ovalbumin (Sigma Chemical, St. Louis, Mo.) was diluted to a concentration of 20 µg/ml in 50 mM Tris-HCl (pH 9.6). 100 microliters/well of this solution was used to coat the wells of high protein binding, microtiter plates (Corning cat. no. 2581) following an overnight incubation at 4° C. The plates were then blocked with 250 microliters PBS/10% FCS for 90 minutes at 37° C. and then rinsed multiple times with PBS/0.5% Tween 20. Serum test samples plus positive and negative control serum antibodies were titrated against PBS/10% FCS over eight 2-fold dilutions. After another 90 minute incubation at 37° C. and multiple washes in PBS/0.5% Tween 20, 100 microliters of a 1:1000 dilution of HRPO-coupled goat anti-murine IgM and goat anti-murine IgG was dispensed into each well. This step was followed by an incubation at 37° C. for 90 minutes, PBS/0.5% Tween 20 washes, and addition of 100 microliters of an ABTS substrate for spectrophotometric detection of antibody activity in the assay. Readings from a spectrophotometer were recorded at 405 nM. The titer of specific antibody in a test serum was assigned as the inverse of the antibody dilution that was equivalent to a half-maximal response. Antibody activity of most sera was saturating at the lowest dilutions, implying a high level of efficiency in the capture and the detection of ovalbumin-specific immunoglobulin.

FIGS. 11A–11F are graphs showing the pattern of lymphokines produced by T cells from aged BALB/c donor mice and younger donor mice. In the study, splenocytes were prepared from groups of 3 mature adult (28 weeks of age) and 3 aged (112 weeks of age) BALB/c donor mice. $1 \times 10^7$ splenocytes were cultured under serum-free conditions in triplicate and activated with 1 µg/ml CD3ε. Culture supernatants were analyzed for the level of IL-2 by quantitative bioassay, and for IL-4, IL-5, γ-IFN, IL-3 and GM-CSF as described above. In the figure, bars represent the mean ±SD for the value of each lymphokine presented.

As seen in FIGS. 11A–11F, the in vitro activation of splenocytes from aged mice under serum-free conditions resulted in a reduced production of some lymphokines and an enhanced production of others, compared to the pattern of lymphokines produced by activated T cells from mature adult mice. Activation-induced production of IL-2, IL-3, and GM-CSF were all significantly reduced in cell cultures from old donors, while the levels of IL-4, IL-5, and γ-IFN were increased above normal adult levels.

A comparison of lymphokine profiles between mature adult and aged mice has been performed using three strains of mice (BALB/c, C57BL/6 and C3H/HeN). The response of each of these strains was analyzed numerous times, and yielded similar results.

Example 9

Preservation of Normal Potential to Produce T-cell Lymphokines and Generate Humoral Immune Responses by Supplementation with DHEA Sulfate Circulating levels of DHEA sulfate declines markedly with advancing age in humans and other mammals. As shown above, direct treatment of T cells from aged or normal murine donors with DHEA prior to activation in vitro augmented their capacity to produce IL-2. In contrast, DHEA-S, the prohormone form of DHEA found principally in the circulation, was shown to have no direct effect on T-cell production of this lymphokine. When DHEA-S was administered to normal mature adults in vivo, it enhanced the potential for IL-2 production by T cells isolated from lymphoid organs having the greatest DHEA-S activity. The most active lymphoid organs are those having anatomic positions downstream from nonmucosal tissues. This example demonstrates that DHEA-S supplementation in vivo can influence the age-related changes in lymphokine production and humoral immune responses.

Groups of adult BALB/c mice, between 35 and 39 weeks of age, were separated into two groups. One group was provided with 100 µg/ml DHEA-S in their drinking water. The hormone was offered ad libitum to these animals. The other group was left untreated. Mice were maintained on oral DHEA-S supplementation until age 114 weeks when they were sacrificed and their spleens individually analyzed for the capacity to produce lymphokines following anti-CD3ε activation. The DHEA-S treated and untreated mice were evaluated by comparing their responses to the lymphokine profile produced by similarly activated splenocytes from mature adult mice (13 weeks of age).

More specifically, splenocytes were prepared from the following groups of BALB/c mice; 2 mature adult (13 weeks of age), 2 aged (114 weeks of age), and 2 aged (114 weeks) receiving 100 µg/ml DHEA-S in their drinking water for the previous 61 weeks. $1 \times 10^7$ splenocytes were cultured under serum-free conditions in triplicate and activated with 1 µg/ml CD3ε. Culture supernatants were analyzed for the level of IL-2 by a quantitative bioassay, and for IL-4, IL-5, γ-IFN, IL-3 and GM-CSF by capture ELISA.

FIGS. 12A–12F are graphs showing the results of DHEA-S supplementation on the capacity of T cells to produce a variety of lymphokines. In FIGS. 12A–12F, bars represent the mean ±SD for the value of each lymphokine presented. It may be seen from FIGS. 12A–12F that DHEA-S supplementation, administered prior to the onset of age-induced decline in immunocompetence, is accompanied by the preservation of normal lymphokine production and development of normal humoral immune responses. DHEA-S supplementation was not only able to preserve normal levels if IL-2, IL-3, and GM-CSF production by activated T cells, but was also able to prevent the age-related increase in γ-IFN, IL-4, and IL-5 production seen in the cell supernatants from untreated aged donors. The results of this study demonstrate that a striking correlation exists between the age-related decline in endogenous DHEA production (plus its metabolites), and the age-associated alterations in T-cell production of lymphokines.

The effect of DHEA-S supplementation on T cell function was also performed using BALB/c, C57BL/6 and C3H/HeN strains of mice. In each test of this experimental approach, lymphokine production by T cells from the treated aged donors had been preserved.

Figure 12A:
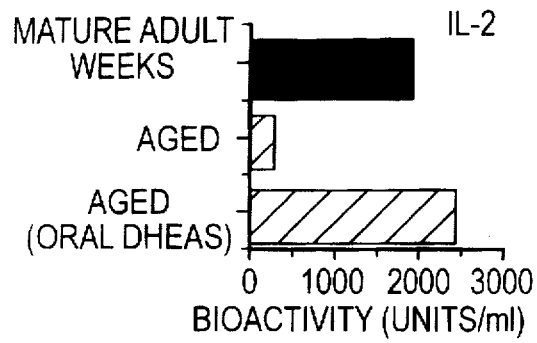
FIG. 12A is a graph showing the results of DHEA-S supplementation on the capacity of T cells from aged mice to produce IL-2.
Figure 12B:
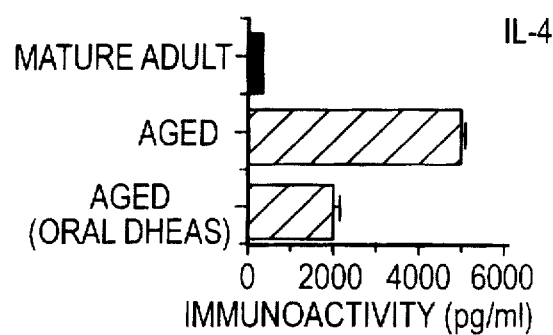
FIG. 12B is a graph showing the results of DHEA-S supplementation on the capacity of T cells from aged mice to produce IL-4.
Figure 12C:
FIG. 12C is a graph showing the results of DHEA-S supplementation on the capacity of T cells from aged mice to produce IL-5.
Figure 12D:
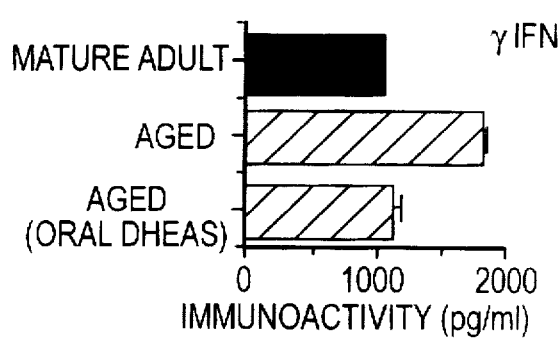
FIG. 12D is a graph showing the results of DHEA-S supplementation on the capacity of T cells from aged mice to produce γ-IFN.
Figure 12E:
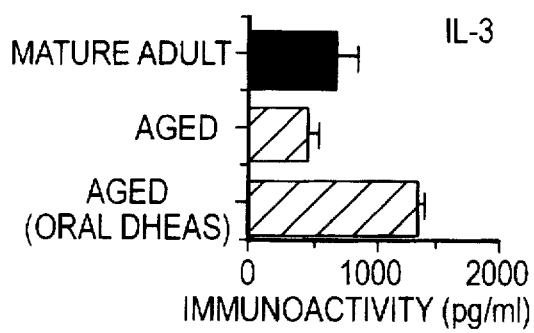
FIG. 12E is a graph showing the results of DHEA-S supplementation on the capacity of T cells from aged mice to produce IL-3.
Figure 12F:
FIG. 12F is a graph showing the results of DHEA-S supplementation on the capacity of T cells from aged mice to produce GM-CSF.
Figure 12G:
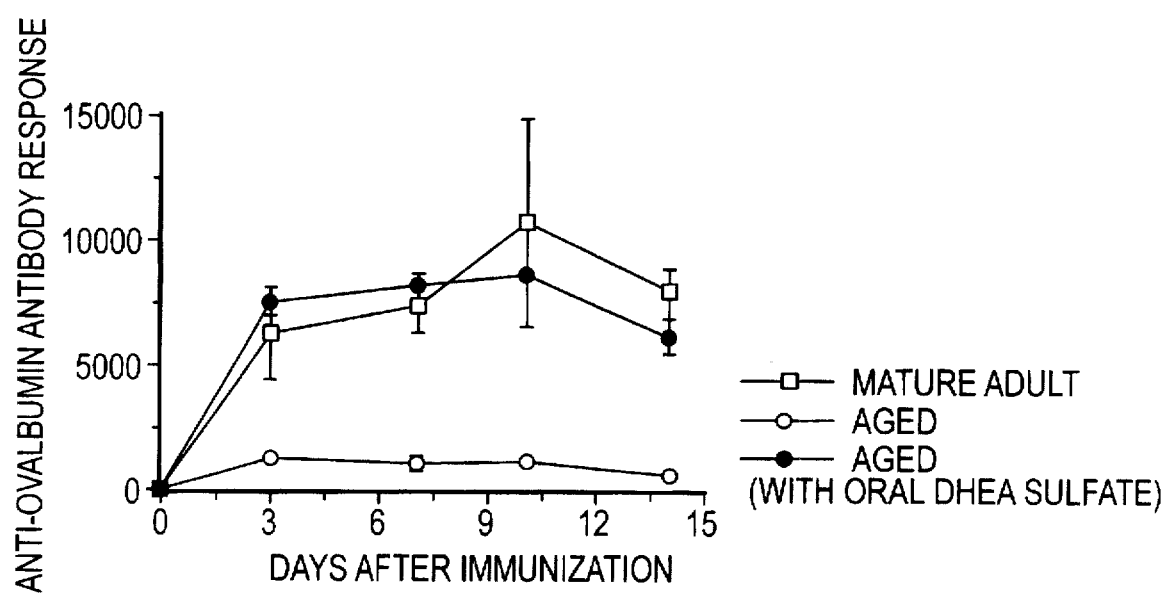
FIG. 12G is a graph showing the results of chronic DHEA-S supplementation on the humoral responsiveness of aged mice to an OVA challenge.

In order to examine the effect of DHEA-S supplementation on the ability of old animals to mount immunologic responses to challenge with foreign protein antigens, the following procedure was used. Groups of 5 mature adult mice (13 weeks of age), 5 aged mice (114 weeks), and 5 aged mice (114 weeks) provided with chronic DHEA-S supplementation (100 µg/ml DHEA-S in their drinking water for the previous 61 weeks, initiated at 8 months of age), were footpad immunized with ovalbumin. The immunization was with 100 µg ovalbumin in a 25 µl volume of Maalox, administered in the hind footpads. All animals were bled on days 0, 3, 5, 7, 10, and 14 post immunization, and individual serum samples analyzed for ovalbumin specific antibody titers by quantitative ELISA, using ovalbumin for capture and HRPO-coupled, goat anti-murine Ig detecting antibodies with specificity for IgM and IgG subclasses. Each ELISA assay was controlled with sera known to be positive or negative for anti-ovalbumin activity. The titer is the inverse of the antibody dilution equal to the half-maximal point on the titration curve. The results of the study, shown in the graph in FIG. 12G, demonstrate that old animals provided with chronic DHEA-S supplementation remain fully capable of rapidly mounting a significant humoral immune response to ovalbumin immunization, with kinetics, titers, and isotype profiles (data not shown), that are almost identical to mature adult controls. As expected, the untreated aged mice responded poorly to a similar antigen challenge, producing predominantly IgM.

Example 10

DHEA-S Administration to Aged Mice Can Reverse Age-Associated Changes in T-cell Lymphokine Production and Their Depressed Humoral Immune Responses to Protein Antigens As shown above, a direct exposure of lymphocytes from aged donors to DHEA in vitro, immediately altered the pattern of lymphokines produced following activation. In addition, we have found that nonmucosal tissue draining lymphoid organs possesses a far greater amount of DHEA sulfatase activity than mucosal tissue draining lymphoid organs. These findings led to the hypothesis that DHEA may be serving as an effector of positional information for lymphocytes residing in certain lymphoid compartments. Any changes in immune function caused by the depressed production of substrate DHEA-S might, therefore, be reversible if DHEA-S is reintroduced in situ. This was examined in the following studies.

Splenocytes were isolated from equal sized groups of mature adult mice (25 weeks of age), aged mice (120 weeks of age), and aged mice given a subcutaneous injection of DHEA-S (100 µg in 100 µl propylene glycol) 24 hours previously. $1 \times 10^7$ splenocytes were cultured under serum-free conditions in triplicate and activated with 1 µg/ml anti-CD3ε. Twenty four hours later, culture supernatants from individual cell cultures were analyzed for the level of IL-2 by a quantitative bioassay, and for IL-4, IL-5, γ-IFN, IL-3 and GM-CSF by capture ELISA. The results, shown in FIGS. 13A–13F, demonstrate that acute replacement therapy with DHEA-S to aged mice restores near normal patterns of T-cell lymphokines within 1 day of treatment. These results strongly suggest that lymphoid cells from old animals exhibit no intrinsic defects. Rather, some of the best documented functional changes to the immune system which accompany aging may be due to the reduced capacity to produce DHEA-S.

Figure 13A:
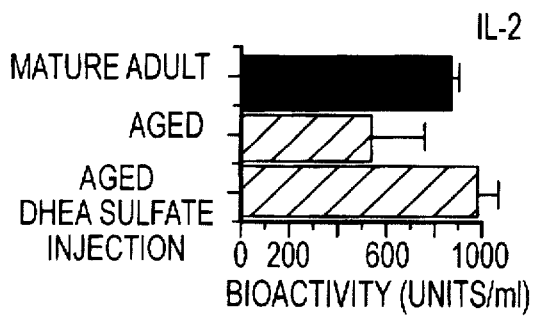
FIG. 13A is a graph showing the results of administration of a bolus of DHEA-S to aged mice on the ability of splenocytes from the treated mice to have restored IL-2 production.
Figure 13B:
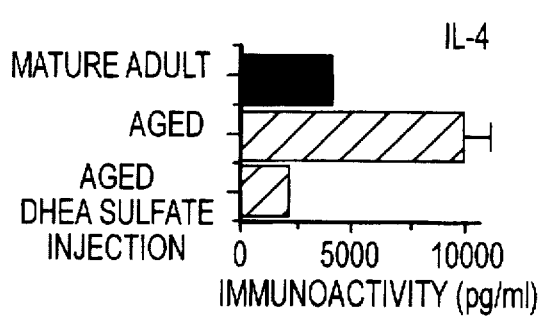
FIG. 13B is a graph showing the results of administration of a bolus of DHEA-S to aged mice on the ability of splenocytes from the treated mice to have restored IL-4 production.
Figure 13C:
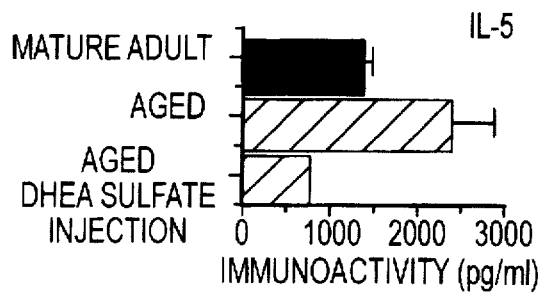
FIG. 13C is a graph showing the results of administration of a bolus of DHEA-S to aged mice on the ability of splenocytes from the treated mice to have restored IL-5 production.
Figure 13D:
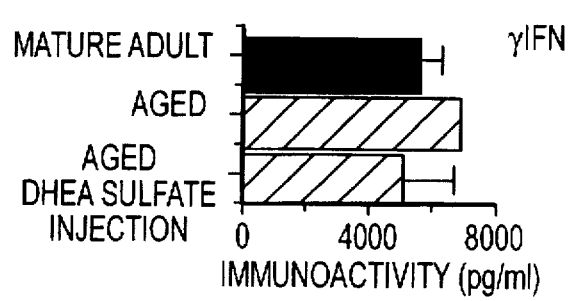
FIG. 13D is a graph showing the results of administration of a bolus of DHEA-S to aged mice on the ability of splenocytes from the treated mice to have restored γ-IFN production.
Figure 13E:
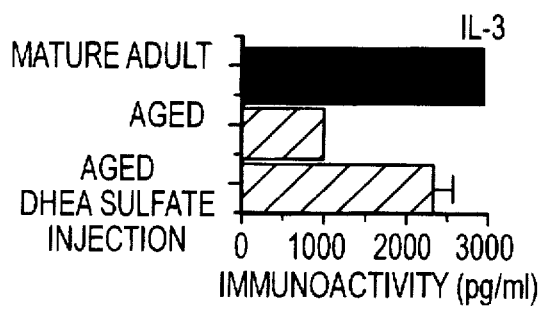
FIG. 13E is a graph showing the results of administration of a bolus of DHEA-S to aged mice on the ability of splenocytes from the treated mice to have restored IL-3 production.
Figure 13F:
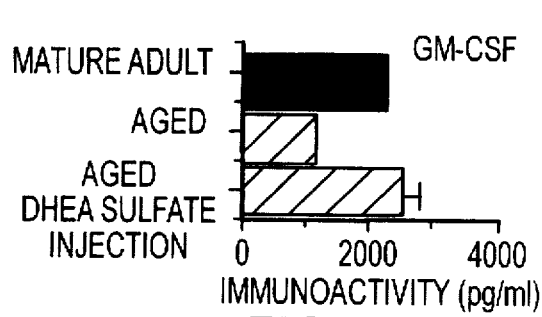
FIG. 13F is a graph showing the results of administration of a bolus of DHEA-S to aged mice on the ability of splenocytes from the treated mice to have restored GM-CSF production.
Figure 13G:
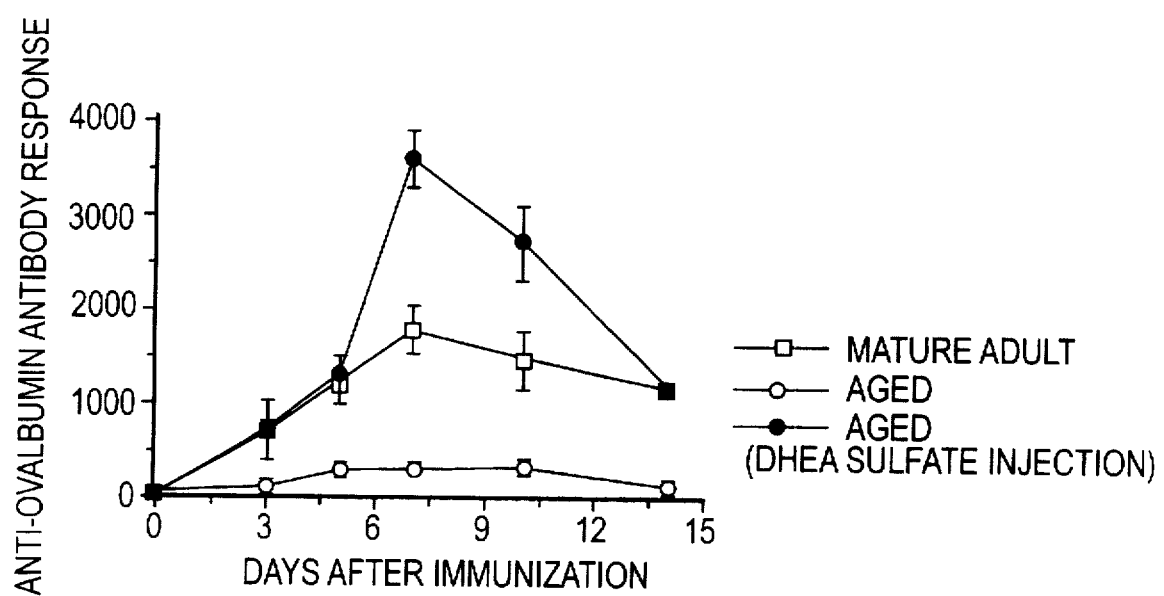
FIG. 13G is a graph showing the results of administration of a bolus of DHEA-S to aged mice on the production of anti-ovalbumin antibodies by the treated mice.

A representative study showing that the administration of a bolus of DHEA-S to aged BALB/c mice restored the capacity of the mice to develop humoral responses is shown in FIG. 13G. In the study, groups of 5 mature adult (25 weeks of age), 5 aged (120 weeks of age), and 5 aged (120 weeks) receiving 100 µg DHEA-S in 100 µl propylene glycol by subcutaneous injection the previous 24 hours were immunized with 100 µg ovalbumin in a 25 µl volume of Maalox, administered in the hind footpads. Sera from individual mice were collected on days 0, 3, 5, 7, 10 and 14 following primary immunization. The titer of anti-ovalbumin antibody was assessed by ELISA using ovalbumin for capture and HRPO-coupled, goat anti-murine Ig detecting antibodies with specificity for IgM and IgG subclasses. Each ELISA assay was controlled with sera known to be positive or negative for anti-ovalbumin activity.

The results in FIG. 13G show that old animals provided with DHEA-S only 24 hours prior to immunization with a foreign protein antigen responded even better than normal mature adults in the production of antibody.

This method of reversing age-related decline in humoral responses has been evaluated twice using BALB/c mice and once with C3H/HeN strains of mice. Similar enhancements in antibody production were achieved in all groups of DHEA-S treated, aged groups of mice.

The results discussed above support the concept that some of the age-associated changes in immune function are extrinsic in cause, and are mediated by the loss in endogenous production of an essential regulatory steroid prohormone.

Example 11

Topical Application of DHEA to Aged Animals Facilitates Chances in the Draining Lymph Node Microenvironment That are Conducive to Successful Immunization Groups of 5 mature adult (13 weeks of age) and 10 aged BALB/c mice (114 weeks of age) were used in the study. All of the aged BALB/c mice received a topical application of 10 µg DHEA in 3.5 µl 95% ethanol to the right hind footpad, 3 hours prior to immunization with 100 µg ovalbumin in a 25 µl volume of Maalox. Five of the aged mice were immunized in the right hind footpad (site identical to the steroid application), and the other 5 immunized in the left hind footpad (site opposite to the steroid application). Sera from individual mice were collected on days 0, 3, 5, 7, 10 and 14 following primary immunization. The titer of anti-ovalbumin antibody was assessed by ELISA using ovalbumin for capture and HRPO-coupled, goat anti-murine Ig detecting antibodies with specificity for IgM and IgG subclasses. Each ELISA assay was controlled with sera known to be positive or negative for anti-ovalbumin activity.

Figure 14:
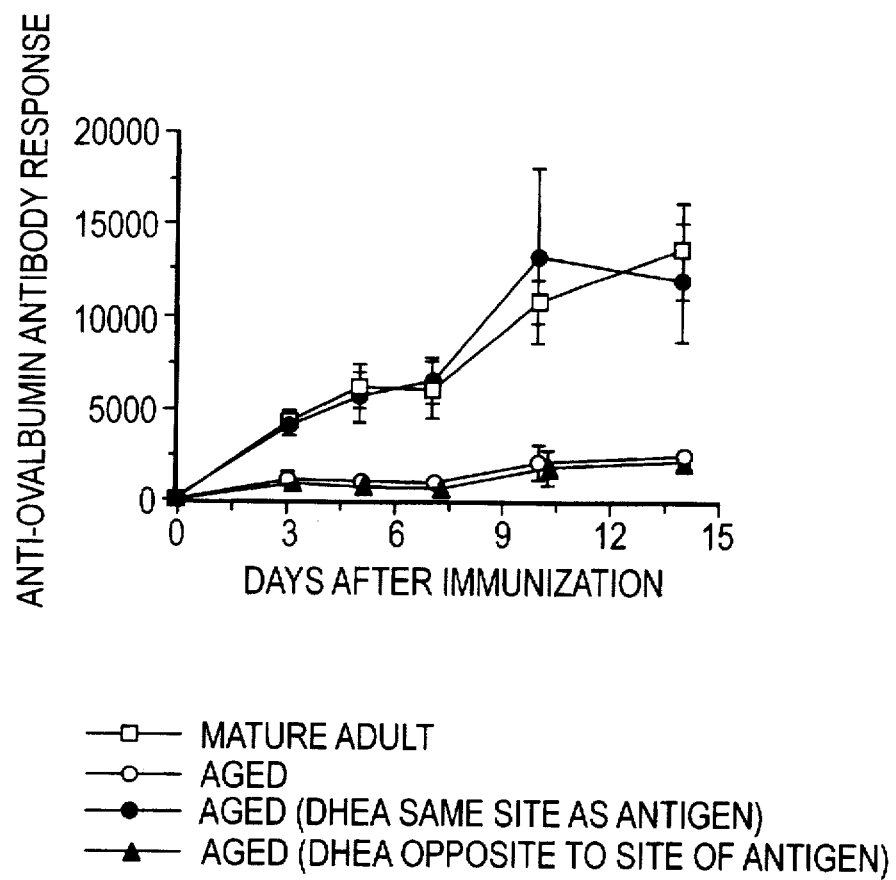
FIG. 14 is a graph showing the effect of topical DHEA application to aged mice on the production of anti-ovalbumin antibodies.

The results, shown in FIG. 14, establish that a topical application of DHEA prior to immunization through the same skin site, provided the aged animals with the ability to generate completely normal humoral immune responses. The untreated group of aged animals, and aged animals provided with topical DHEA on the footpads opposite the site of immunization, responded quite poorly to immunization, with minimal antibody being observed.

The results of reversing the age-related decline in humoral responses has been repeated with BALB/c mice, and with C3H/HeN strain of mice.

These results establish that the pronounced lymphoid organ-specific changes in the types of lymphokines produced by T cells from aged animals given topical DHEA, can be paralleled by an equally dramatic enhancement in ability to generate potent humoral immune responses to challenge with a foreign antigen protein.

Example 12

Lymphokine Production and Contact Hypersensitivity Responses are Modulated in Thermally-Injured Mice Some of the most profound immunological changes that appear as a result of thermal injury are both rapid loss in the ability to develop cellular immune responses of several types and an inability of activated T lymphocytes to produce IL-2 and γ-IFN. In order to establish the effect on IL-4, the production of this lymphokine by T lymphocytes from thermally-injured and control mice was examined.

Six to eight 8 week old BALB/c mice were shaved on their dorsal surface surfaces as a preparation for receiving a thermal injury. Two days after removal of truncal fur, all of the experimental mice were anaesthetized, and half were given a 20% total body surface area (TBSA), full- thickness scald burn. Following revival from anesthesia, the burned mice were fluid resuscitated over a 3-day period using normal saline. Both thermally-injured and control groups of mice were allowed to feed and drink normally for 5 days, at which time all animals were sacrificed. Splenocytes from individual thermally-injured and control mice were prepared for culture in serum-free media. $1 \times 10^7$ cells was dispensed, in triplicate, into 24-well culture plates with or without 1.5 µg monoclonal anti-CD3ε. Culture plates were incubated in a 38° C., 10% $CO_2$, humidified chamber for 24 hours prior to collection of cell-free supernatants for quantitative evaluation of IL-2, γ-IFN, and IL-4. Assays for each of these lymphokines was as described above.

Figure 15A:
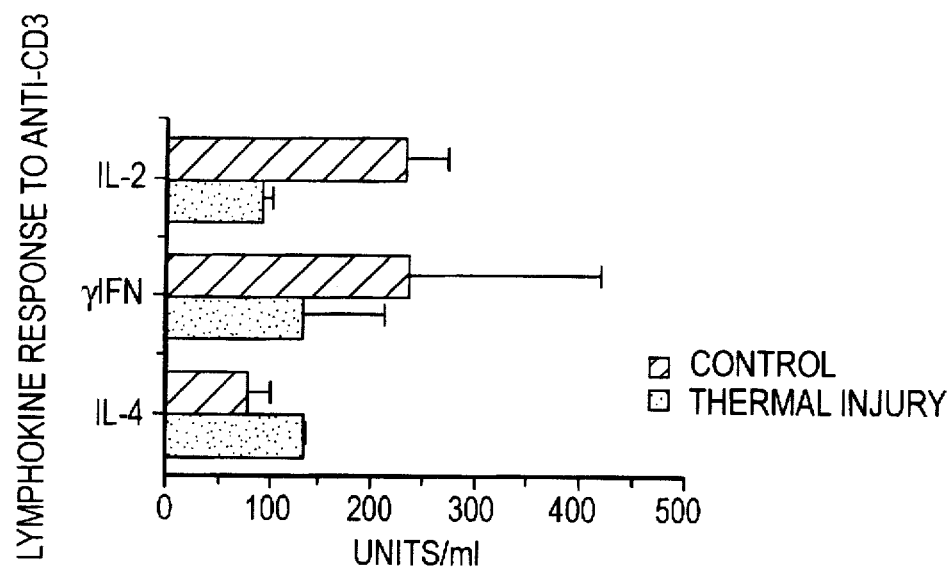
FIG. 15A is a graph showing the effect of thermal injury on the production of lymphokines by activated T-cells.

The effect of the thermal injury on lymphokine production is shown in FIG. 15A. The results on the depressed production of IL-2 and γ-IFN agrees with other reports on humans and rodents. In contrast to this observed depression in IL-2 and γ-IFN levels, activated T cells from thermally-injured mice were found to produce a greater amount of IL-4, as compared to activated splenocytes isolated from control mice.

Because thermal injury is known to compromise development of contact hypersensitivity responses, groups of thermally-injured (20% TBSA) and control mice were contact sensitized to DNFB to demonstrate that the thermal injury protocol, in addition to reducing the capacity of activated T cells to produce IL-2 and γ-IFN, also results in a reduced ability of injured mice to develop cellular immune responses. Five days after receiving a 20% TBSA, equivalent groups of normal and thermally-injured mice were sensitized by the application of DNFB to their shaved abdomens. All experimental animals were challenged 4 days later by topical applications of DNFB to the right hind footpad. The intensity of the hypersensitivity reaction was determined by quantitating the difference between thicknesses of the challenged and the unchallenged footpad.

Figure 15B:
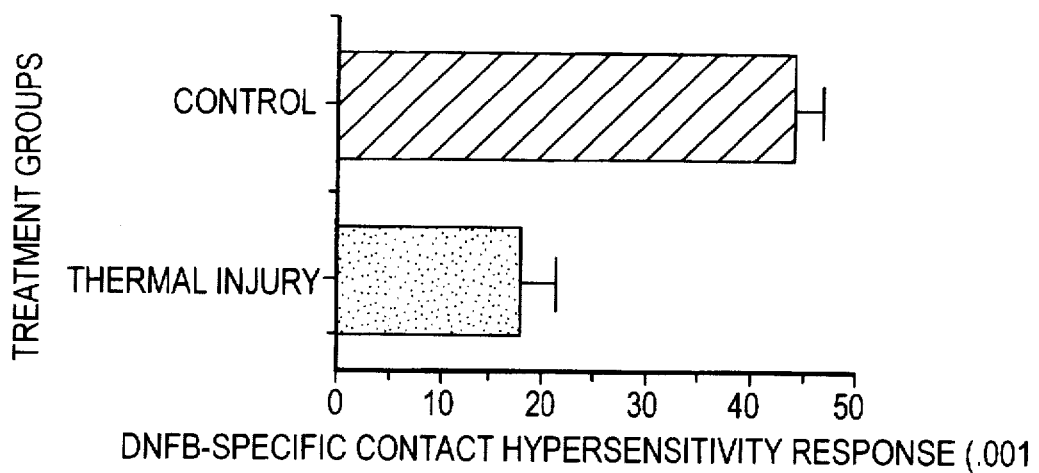
FIG. 15B is a graph showing the effect of thermal injury on contact hypersensitivity reactions.
Figure 16A:
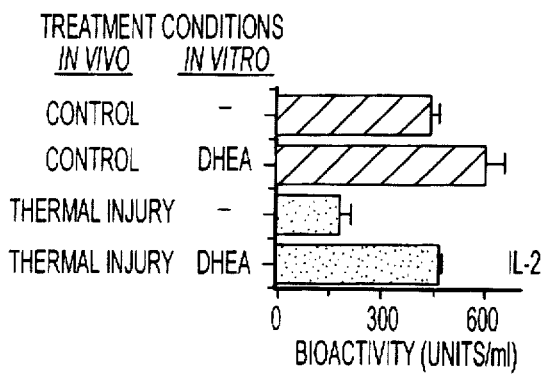
FIG. 16A is a graph showing the effect of DHEA treatment in vitro on the production of IL-2 by activated splenocytes from thermally injured and control mice.
Figure 16B:
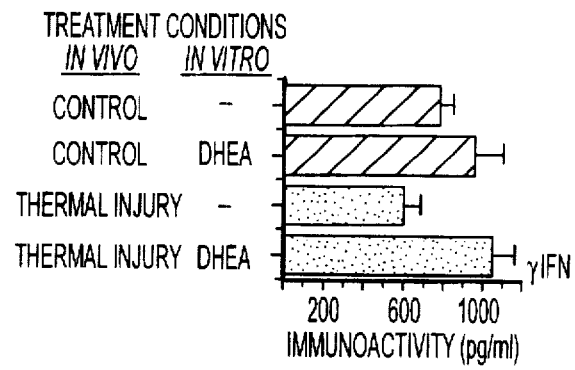
FIG. 16B is a graph showing the effect of DHEA treatment in vitro on the production of γ-IFN by activated splenocytes from thermally injured and control mice.
Figure 16C:
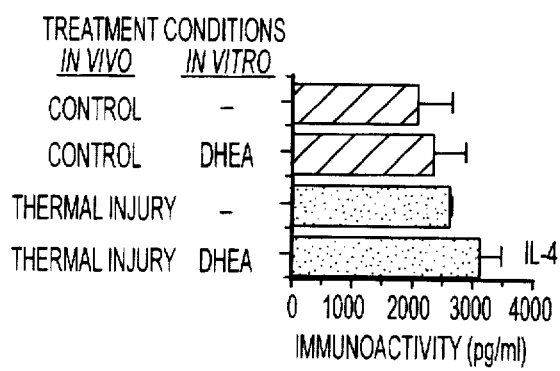
FIG. 16C is a graph showing the effect of DHEA treatment in vitro on the production of IL-4 by activated splenocytes from thermally injured and control mice.
Figure 16D:
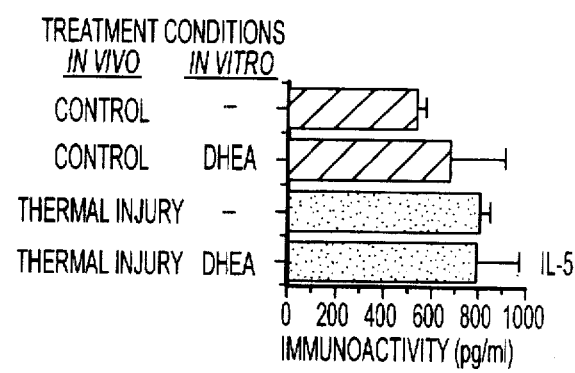
FIG. 16D is a graph showing the effect of DHEA treatment in vitro on the production of IL-5 by activated splenocytes from thermally injured and control mice.
Figure 16E:
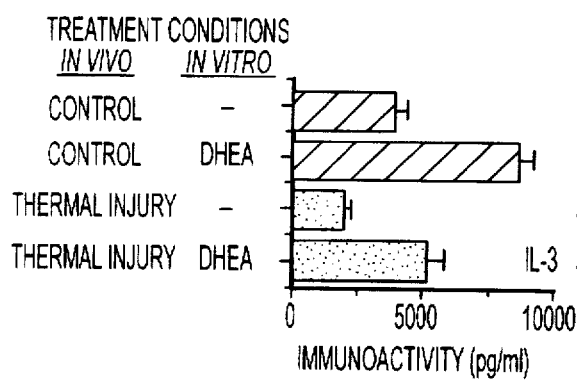
FIG. 16E is a graph showing the effect of DHEA treatment in vitro on the production of IL-3 by activated splenocytes from thermally injured and control mice.
Figure 16F:
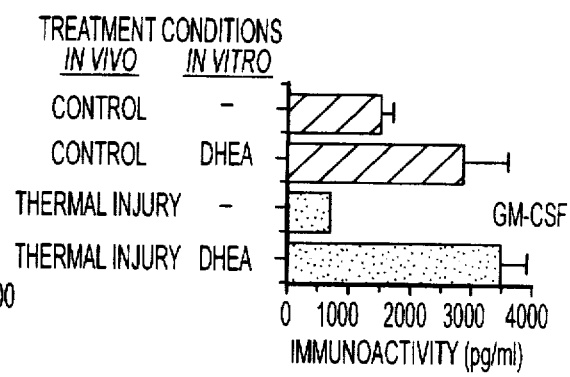
FIG. 16F is a graph showing the effect of DHEA treatment in vitro on the production of GM-CSF by activated splenocytes from thermally injured and control mice.
Figure 17A:
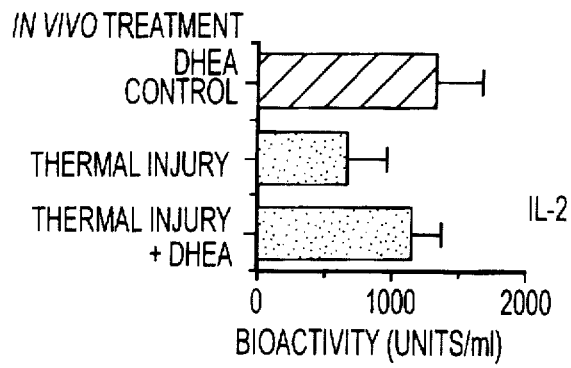
FIG. 17A is a graph showing the effect of DHEA treatment in vivo on the production of IL-2 by activated splenocytes from thermally injured and control mice.
Figure 17B:
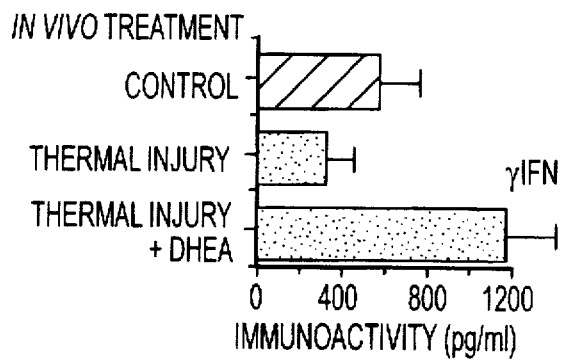
FIG. 17B is a graph showing the effect of DHEA treatment in vivo on the production of γ-IFN by activated splenocytes from thermally injured and control mice.
Figure 17C:
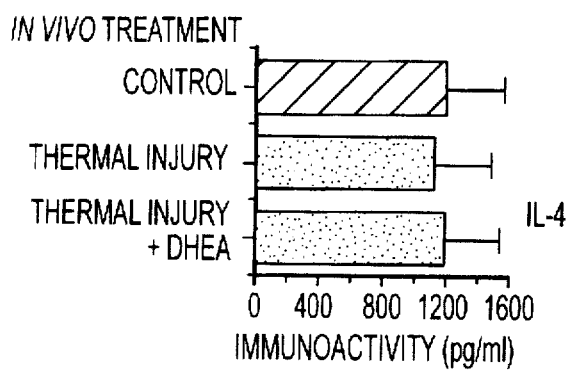
FIG. 17C is a graph showing the effect of DHEA treatment in vivo on the production of IL-4 by activated splenocytes from thermally injured and control mice.
Figure 17D:
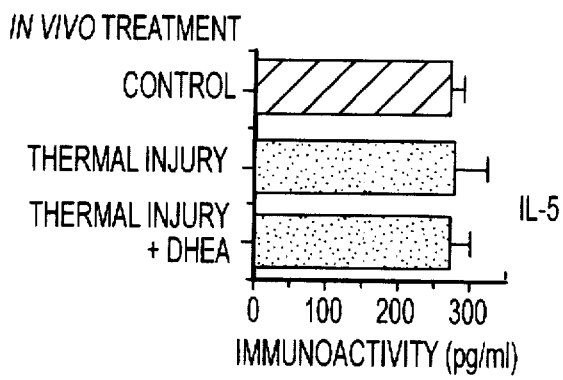
FIG. 17D is a graph showing the effect of DHEA treatment in vivo on the production of IL-5 by activated splenocytes from thermally injured and control mice.
Figure 17E:
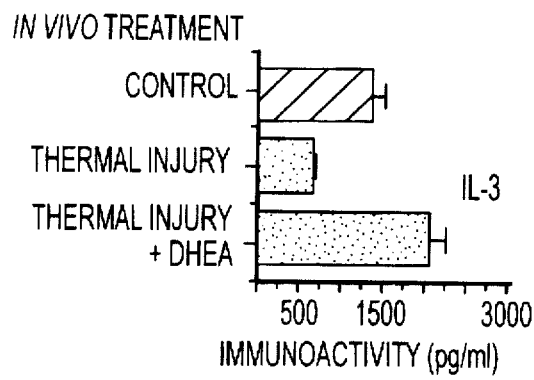
FIG. 17E is a graph showing the effect of DHEA treatment in vivo on the production of IL-3 by activated splenocytes from thermally injured and control mice.
Figure 17F:
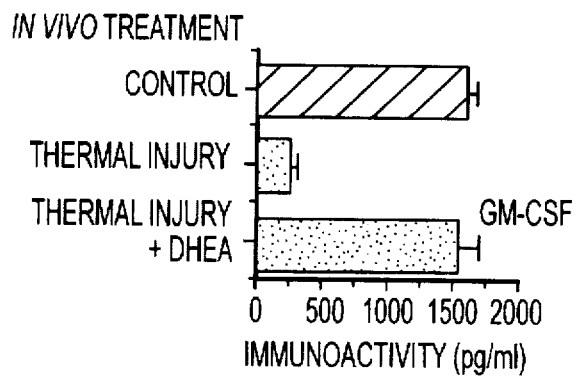
FIG. 17F is a graph showing the effect of DHEA treatment in vivo on the production of GM-CSF by activated splenocytes from thermally injured and control mice.

FIG. 15B shows the results of the DNFB challenge studies (the bars represent the mean ±SEM). The results confirm that the development of contact sensitivity responses and production of the lymphokines which are associated with promoting these responses are depressed in mice given a 20% TBSA, full-thickness scald burn. Furthermore, the ability of T cells to produce the lymphokine, IL-4, which promotes B-cell differentiation, immunoglobulin isotype-switching, and also potent anti-inflammatory activity, is not apparently depressed as a result of thermal injury. These findings suggest that thermal injury is a selective modulator of T-cell function.

Example 13

Treatment in vitro of Splenocytes from Thermally-Injured Mice with DHEA Restores the Capacity to Produce Lymphokines The following study was performed in order to evaluate whether the exposure of T cells from thermally-injured mice to DHEA would influence their capacity to produce lymphokines subsequent to activation. Groups of 4 to 6 BALB/c mice were either thermally injured with a 20% TBSA scald burn or were non-injured controls. Five days after thermal injury, the time when the "immunosuppression" is maximal, all surviving mice were sacrificed and splenocytes from individual mice were prepared for culture in serum-free media. Splenocytes were seeded into 24-well macroculture plates at $1 \times 10^7$ cells/ml/well. Parallel cultures from each mouse were sham or DHEA pulsed at $10^{-7}$M for 60 minutes, washed multiple times to remove nonbound steroid, and then were incubated in serum-free medium and were either unstimulated or stimulated with 1.5 µg anti-CD3ε. Following a 24-hour incubation period, cell-free supernatants were quantitatively analyzed for IL-2 using the standard HT-2 bioassay, and for γ-IFN, IL-4, IL-5, IL-3, and GM-CSF by capture Elisa. The results are shown in FIGS. 16A–16F, where the bars represent the ±standard deviation for each lymphokine.

As seen from FIGS. 16A–16F, a comparison between lymphokines produced by activated splenocytes from thermally-injured and control animals indicates that thermal injury causes a depression in the capacity of activated T cells to secrete IL-2, γ-IFN, IL-3, and GM-CSF. Only minimal changes (elevations) in the quantities of IL-4 and IL-5 were observed. The treatment of T cells from the thermally-injured animals with DHEA reversed the inhibitory effect on IL-2, γ-IFN, IL-3, and GM-CSF production; the values of these lymphokines returned to near control levels. The DHEA treatment had no effect on IL-4 or IL-5 production.

Example 14

Treatment in vivo of Thermally Injured Mice with DHEA Preserves Normal Immune Function The following study illustrates that the direct administration of DHEA to mice shortly after thermal injury influences their levels of immunocompetence.

Groups of 12 thermally-injured and 6 control BALB/c mice were established as described above. After subjecting the mice to a 20% TBSA scald burn, six of the thermally-injured mice were given a subcutaneous injection of 100 µg DHEA in a propylene glycol carrier. All remaining animals received the carrier alone. Five days later, all surviving mice were sacrificed and their splenocytes were individually prepared for culture, and activated with anti-CD3ε to induce lymphokine secretion. Culture supernatants were collected 24 hours after activation and evaluated for lymphokine content, as described above. The results of the study are presented in FIGS. 17A–17F, where the bars represent mean ±SD for each value. As seen in FIGS. 17A–17F, DHEA directly influences IL-2, γ-IFN, IL-3, and GM-CSF production by T cells isolated from thermally-injured mice. The administration of a single bolus injection of DHEA (100 µg) 1 hour after thermal injury was sufficient to preserve for at least 5 days a normal capacity by their lymphocytes to produce IL-2, γ-IFN, IL-3, and GM-CSF following activation. No significant changes from normal were observed in the levels of IL-4 and IL-5 made by activated lymphoid cells from these animals.

Figure 18:
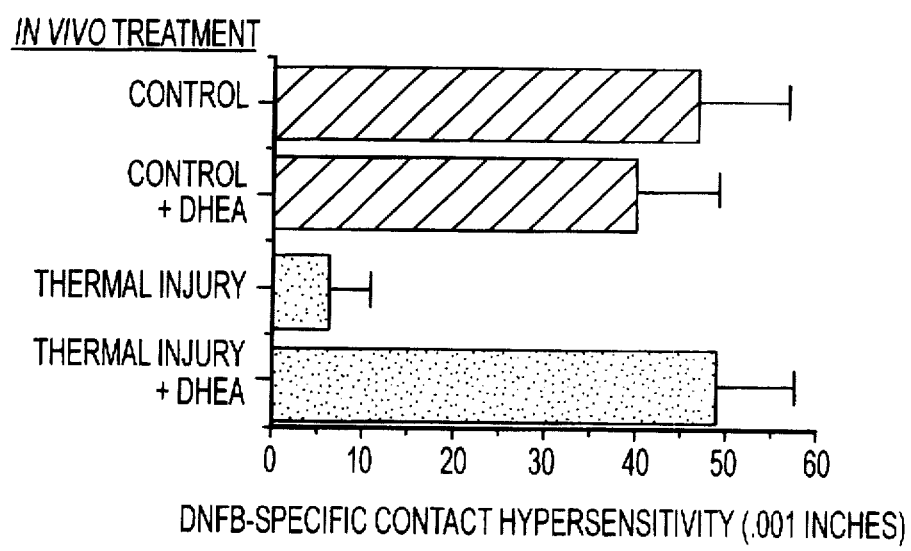
FIG. 18 is a graph showing the effect of DHEA treatment in vivo on contact hypersensitivity responses of thermally injured and control mice.

The effect of DHEA treatment in vivo on the animals' development of cellular immune responses was examined. Parallel groups of thermally-injured and control mice were either given 100 µg DHEA in propylene glycol carrier or the carrier alone 1 hour post burn. These animals were contact sensitized 5 days later by administration of DNFB on the abdomen. Challenge doses of DNFB to the right footpads were applied 4 days later. The differences in thickness between the right (challenged) and the left (unchallenged) footpads were used to quantitate the contact hypersensitivity responses. The results are shown in FIG. 18; the bars represent mean ±SD for each group of mice. As shown in FIG. 18, the intensity of the contact hypersensitivity responses elicited by thermally-injured mice are markedly depressed as compared to controls. The administration of DHEA to thermally-injured mice was found to completely preserve the ability of these animals to develop contact hypersensitivity responses of normal intensity.

We conclude from these studies that DHEA treatment post burn is an effective therapy for preserving the capacity of T-lymphocytes from thermally-injured animals to produce normal quantities of a number of lymphokines, especially those that are essential for development of cellular immune responses. This finding is supported by the additional demonstration that DHEA-treated thermally-injured mice also retain their capacity to develop normal contact hypersensitivity responses.

Example 15

DHEA Treatment in vivo Promotes Resistance to Infection by L. monocytogenes in Thermally Injured Mice This study addresses the utility of DHEA therapy post burn in preserving resistance to a bacterial infection. C3H/HeN strain mice are inherently resistant to infection by the gram positive intracellular pathogen, L. monocytogenes. However, thermal injury results in an increased susceptibility to this pathogen. Therefore, a switch from "resistant" to a more "susceptible" phenotype provides a model system to evaluate the effect of DHEA on preserving the "resistant" phenotype in thermally-injured animals.

Figure 19:
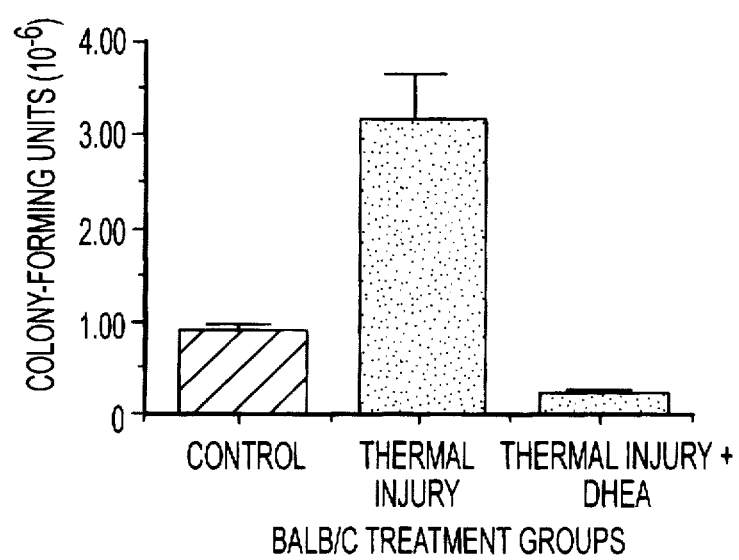
FIG. 19 is a graph showing the effect of DHEA treatment on resistance to *L. monocytogenes* in control and thermally injured C3H mice.

Normal (control) and thermally-injured mice were prepared as described above. Half of the thermally-injured mice received a single bolus injection of 100 µg DHEA subcutaneously within 1 hour after thermal injury. Three days later, all mice were infected with $2 \times 10^6$ viable L. monocytogenes organisms, and 3 days after infection the mice were sacrificed and homogenates of individual spleens were prepared. The number of colonies of L. monocytogenes per spleen were evaluated using standard methodology, and scored. The results are presented graphically in FIG. 19, where the bars represent means ±SEM for each treatment group. The results indicate that thermal injury enhances the susceptibility of the C3H strain mice to infection by L. monocytogenes. Of consequence, DHEA treatment of burned animals not only preserves the resistant phenotype, but surprisingly, the level of resistance to infection is actually enhanced by DHEA treatment over that observed in the control group.

Example 16

Figure 20:
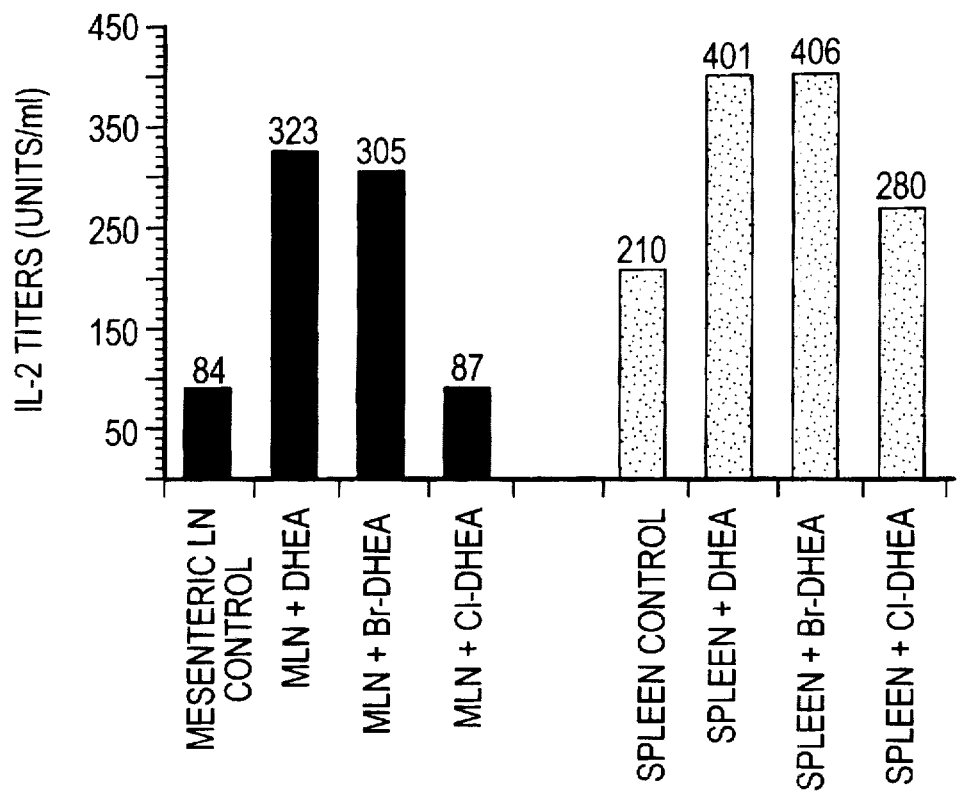
FIG. 20 is a graph showing the effect of DHEA, 16α-bromo-DHEA and 16α-chloro-DHEA in vitro on IL-2 production by lymphocytes from aged mice.

The Effect of 16α-bromo-DHEA and 16α-chloro-DHEA on Age-Associated Changes in T-cell Lymphokine Production In order to demonstrate the effectiveness of the cogeners of DHEA, 16α-bromo-DHEA and 16α-chloro-DHEA on age-associated changes in T-cell lymphokine production, the following study was performed. Suspensions containing T cells were prepared from the mesenteric lymph node and from the spleen of groups of aged (old) mice. The T cell suspensions were exposed in vitro to DHEA, 16α-bromo-DHEA or 16α-chloro-DHEA at a concentration of $10^{-7}$M for 60 minutes. After activation with anti-CD3ε, the IL-2 titers in the cell-free supernatants was measured by bioassay. The results, shown in FIG. 20, indicate that 16α-bromo-DHEA is as active as DHEA in restoring IL-2 production by the activated T-cells. However, surprisingly, 16α-chloro-DHEA had little, if any, effect on restoring IL-2 production.

Example 17

Figure 21:
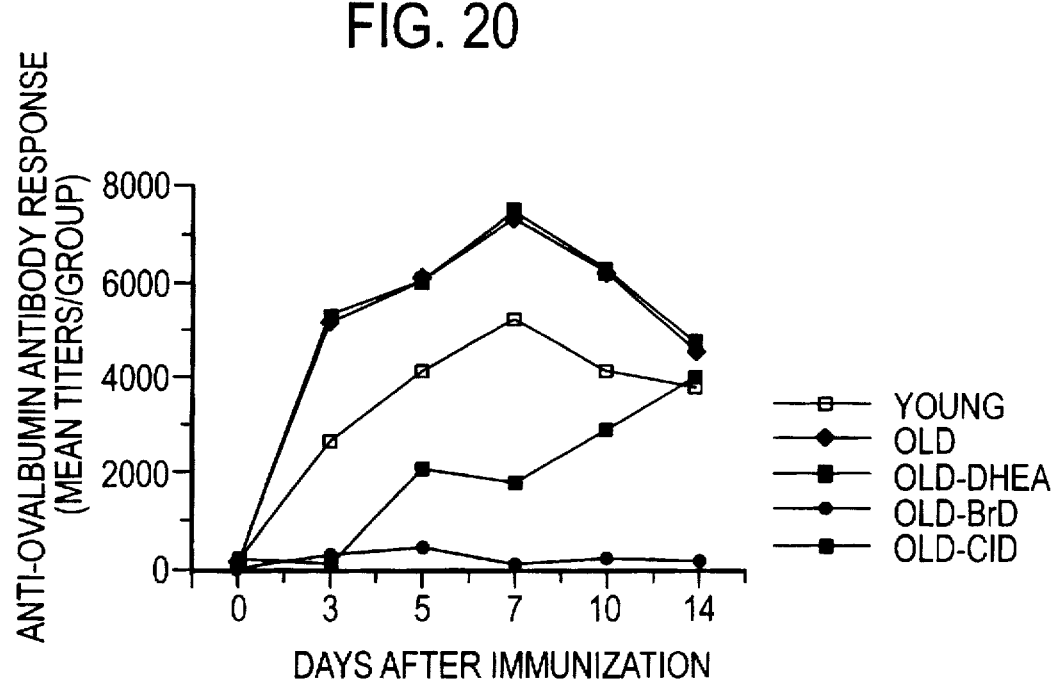
FIG. 21 is a graph showing the effect of topically applied DHEA 16α-bromo-DHEA and 16α-chloro-DHEA on the anti-Ovalbumin antibody response in aged mice.

The Effect of 16α-bromo-DHEA and 16α-chloro-DHEA on the Depressed Humoral Immune Responses of Aged Mice to Protein Antigens The effectiveness of the cogeners of DHEA, 16α-bromo-DHEA and 16α-chloro-DHEA on age-associated changes in the humoral immune response is demonstrated in the following study. Groups of mature (young) and aged (old) mice were treated by topical administration of 10 µg of DHEA, 16α-bromo-DHEA, or 16α-chloro-DHEA. Three hours subsequent to treatment, the treated and control animals were subjected to an ovalbumin (OVA) challenge as described in the Examples above, and the anti-ovalbumin antibody response was measured at 0, 3, 5, 7, 10, and 14 days after immunization. The results, shown in FIG. 21, indicate that 16α-bromo-DHEA (BrD) is as effective as DHEA in restoring humoral immune responsiveness. The chlorinated cogener, 16α-chloro-DHEA (ClD) yielded a lower, but significant effect on antibody production.

Example 18

Dose-dependent Inhibition of IL-2 and γ-IFN with a Simultaneous Activation of IL-4 by Glucocorticoids and 1,25 Dihydroxy Vitamin $D_3$ This experiment demonstrates that glucocorticosteroids and 1,25-dihydroxy vitamin $D_3$, at physiological dose levels, enhance the production of IL-4 without affecting IL-2 and IFN production, and, at pharmacological dose levels, enhance the production of IL-4 and inhibit the production of IL-2 and γ-IFN. (C3H×BL/6)$F_1$ mice were immunized by subcutaneous immunization in the flank region with 100 μg OVA/CFA. Two weeks later, single cell suspensions of spleens were prepared in Nutridoma-supplemented, complete RPMI at 1×10$^7$ cells/ml. Referring to FIG. 22A, a portion of the cells was subdivided into groups containing the indicated concentrations of DEX and incubated for 30 minutes at 37° C. Referring to FIG. 22B, cells were treated with corticosterone. Referring to FIG. 22C, cells were treated with 1,25-dihydroxy vitamin $D_3$. After multiple washes, cells were dispensed into culture wells in 1 ml volumes at 1×10$^7$ cells/ml with either no antigen or 100 μg OVA. After a 24-hour incubation period in a humidified $CO_2$ incubator, the culture supernatants were harvested for assessment of IL-2 and IL-4 activity using a modification of the method of Mosmann (*J Immunol. Meth.*, 65:55(1983)). γ-IFN was evaluated using a modification of the method of Green (Green et al., *J Clin. Microbiol.*, 12:433 (1980)). All groups cultured without antigen produced less than 1 unit IL-2 or IL-4 and no detectable γ-IFN.

We claim:

1. A method for selectively augmenting a vaccine-induced protective immune response which comprises administering a vaccine comprising an immunizing agent and a vaccine adjuvant wherein said immunizing agent does not contain a lethal dose of virus and said vaccine adjuvant is DHEAS or 16α-bromo-DHEAS.

2. The method of claim 1 wherein said adjuvant is administered 3 hours or less prior to the immunizing agent.

3. The method of claim 1 wherein said adjuvant is administered contemporaneously with the immunizing agent.

4. The method of claim 1 wherein said adjuvant is administered topically.

5. The method of claim 1 wherein said adjuvant is administered by injection.

6. The method of claim 1 wherein the adjuvant is mixed with the immunizing agent prior to administration.

7. The method of claim 1 wherein the immunizing agent and the adjuvant are administered such that they drain to the same lymph nodes.

8. The method of claim 2 wherein the immunizing agent and adjuvant are administered such that they drain to the same lymph nodes.

9. The method of claim 3 wherein the immunizing agent and adjuvant are administered such that they drain to the same lymph nodes.

10. The method of claim 1 wherein said adjuvant is DHEAS.

11. The method of claim 1 wherein said adjuvant is 16α-bromo-DHEAS.

12. A method for selectively augmenting a vaccine-induced protective immune response which comprises administering a vaccine comprising an immunizing agent and a vaccine adjuvant wherein said immunizing agent does not contain a lethal dose of virus and said vaccine adjuvant is 1,25-dihydroxy vitamin $D_3$.

13. The method of claim 12 wherein said adjuvant is administered 3 hours or less prior to the immunizing agent.

14. The method of claim 12 wherein said adjuvant is administered contemporaneously with the immunizing agent.

15. The method of claim 12 wherein said adjuvant is administered topically.

16. The method of claim 12 wherein said adjuvant is administered by injection.

17. The method of claim 12 wherein the adjuvant is mixed with the immunizing agent prior to administration.

18. The method of claim 12 wherein the immunizing agent and the adjuvant are administered such that they drain to the same lymph nodes.

19. The method of claim 13 wherein the immunizing agent and adjuvant are administered such that they drain to the same lymph nodes.

20. The method of claim 14 wherein the immunizing agent and adjuvant are administered such that they drain to the same lymph nodes.

21. A method for selectively augmenting a vaccine-induced protective immune response which comprises administering a vaccine comprising an immunizing agent and a vaccine adjuvant wherein said immunizing agent does not contain a lethal dose of virus and said vaccine adjuvant is a mixture of 1,25-dihydroxy vitamin $D_3$ and at least one compound selected from the group consisting of DHEA, 16α-bromo-DHEA, DHEAS and 16α-bromo-DHEAS.

22. The method of claim 21 wherein said compound is DHEA.

23. The method of claim 21 wherein said compound is 16α-bromo-DHEA.

24. The method of claim 21 wherein said compound is DHEAS.

25. The method of claim 21 wherein said compound is 16α-bromo-DHEAS.

26. An immunizing composition which comprises an effective amount of an immunizing agent and a vaccine adjuvant wherein said immunizing agent does not contain a lethal dose of a virus and said vaccine adjuvant is DHEAS or 16α-bromo-DHEAS.

27. The composition of claim 26 wherein said vaccine adjuvant is DHEAS.

28. The composition of claim 26 wherein said vaccine adjuvant is 16-α-bromo-DHEAS.

* * * * *